(12) United States Patent
Atalar et al.

(10) Patent No.: US 6,898,454 B2
(45) Date of Patent: May 24, 2005

(54) SYSTEMS AND METHODS FOR EVALUATING THE URETHRA AND THE PERIURETHRAL TISSUES

(75) Inventors: Ergin Atalar, Columbia, MD (US); Harald Hartmann Quick, Essen-Werden (DE); Parag Karmarkar, Elliot City, MD (US)

(73) Assignees: The Johns Hopkins University, Baltimore, MD (US); Surgi-Vision, Inc., Marietta, GA (US)

( * ) Notice: Subject to any disclaimer, the term of this patent is extended or adjusted under 35 U.S.C. 154(b) by 506 days.

(21) Appl. No.: 09/824,536

(22) Filed: Apr. 2, 2001

(65) Prior Publication Data
US 2002/0040185 A1 Apr. 4, 2002

Related U.S. Application Data

(63) Continuation-in-part of application No. 09/817,893, filed on Mar. 26, 2001, now Pat. No. 6,628,980, which is a continuation-in-part of application No. 09/549,921, filed on Apr. 14, 2000, now Pat. No. 6,549,800, which is a continuation-in-part of application No. 09/536,090, filed on Mar. 24, 2000, now Pat. No. 6,675,033, which is a continuation-in-part of application No. 09/360,144, filed on Jul. 26, 1999, now abandoned, which is a continuation-in-part of application No. 09/191,563, filed on Nov. 13, 1998, now Pat. No. 6,263,229, which is a continuation-in-part of application No. 08/638,934, filed on Apr. 25, 1996, now Pat. No. 5,928,145.
(60) Provisional application No. 60/194,060, filed on Mar. 31, 2000.

(51) Int. Cl.⁷ ................................................. A01B 5/05
(52) U.S. Cl. ..................................................... 600/410
(58) Field of Search ............................... 600/410, 411, 600/407, 422, 423, 421; 324/307, 308, 309; 128/653.3

(56) References Cited

U.S. PATENT DOCUMENTS

| | | | |
|---|---|---|---|
| 3,342,175 A | 9/1967 | Bulloch | 128/2 |
| 4,430,076 A | 2/1984 | Harris | 604/96 |
| 4,431,005 A | 2/1984 | McCormick | 128/656 |
| 4,445,501 A | 5/1984 | Bresler | 128/1.5 |

(Continued)

FOREIGN PATENT DOCUMENTS

| | | |
|---|---|---|
| EP | 0 466 424 A1 | 1/1992 |
| EP | 0 557 127 A2 | 8/1993 |
| EP | 0 659 385 A1 | 6/1995 |
| EP | 0 673 621 A1 | 9/1995 |
| EP | 0 557 127 A3 | 3/1996 |
| EP | 0 768 539 A2 | 4/1997 |
| EP | 0 908 739 A2 | 4/1999 |
| WO | WO 99/27390 | 6/1999 |
| WO | WO 00/64003 | 10/2000 |

OTHER PUBLICATIONS

Fielding, Julia R. et al., "MR Imaging of the Female Pelvic Floor in the Supine and Upright Positions", Journal of Magnetic Resonance Imaging 6: 961–963 (1996).

(Continued)

*Primary Examiner*—Daniel Robinson
(74) *Attorney, Agent, or Firm*—Foley Hoag LLP; Scott E. Kamholz

(57) ABSTRACT

The present invention provides systems and methods for the evaluation of the urethra and periurethral tissues using an MRI coil adapted for insertion into the male, female or pediatric urethra. The MRI coil may be in electrical communication with an interface circuit made up of a tuning-matching circuit, a decoupling circuit and a balun circuit. The interface circuit may also be in electrical communication with a MRI machine. In certain practices, the present invention provides methods for the diagnosis and treatment of conditions involving the urethra and periurethral tissues, including disorders of the female pelvic floor, conditions of the prostate and anomalies of the pediatric pelvis.

62 Claims, 12 Drawing Sheets

U.S. PATENT DOCUMENTS

| | | | |
|---|---|---|---|
| 4,572,198 A | 2/1986 | Codrington | 128/653 |
| 4,643,186 A | 2/1987 | Rosen et al. | 1289/303.1 |
| 4,672,972 A | 6/1987 | Berke | 128/653 |
| 4,766,381 A | 8/1988 | Conturo et al. | 324/309 |
| 4,776,341 A | 10/1988 | Bachus et al. | 128/653 |
| 4,791,372 A | 12/1988 | Kirk et al. | 324/318 |
| 4,793,356 A | 12/1988 | Misic et al. | 128/653 |
| 4,812,761 A * | 3/1989 | Vaughan, Jr. | 324/307 |
| 4,813,429 A | 3/1989 | Eshel et al. | 128/736 |
| 4,823,812 A | 4/1989 | Eshel et al. | 128/804 |
| 4,858,613 A | 8/1989 | Fry et al. | 128/660.03 |
| 4,897,604 A | 1/1990 | Carlson et al. | 324/318 |
| 4,922,204 A | 5/1990 | Duerr et al. | 324/322 |
| 4,932,411 A | 6/1990 | Fritschy et al. | 128/653 A |
| 4,960,106 A | 10/1990 | Kubokawa | 128/6 |
| 5,019,075 A | 5/1991 | Spears et al. | 606/7 |
| 5,035,231 A | 7/1991 | Kubokawa et al. | 128/6 |
| 5,050,607 A | 9/1991 | Bradley et al. | 128/653 A |
| 5,090,959 A | 2/1992 | Samson et al. | 604/96 |
| 5,095,911 A | 3/1992 | Pomeranz | 128/662.06 |
| 5,099,208 A | 3/1992 | Fitzpatrick et al. | 324/312 |
| 5,167,233 A | 12/1992 | Eberle et al. | 128/662.06 |
| 5,170,789 A | 12/1992 | Narayan et al. | 128/653.5 |
| 5,190,046 A | 3/1993 | Shturman | 128/662.06 |
| 5,211,165 A | 5/1993 | Dumoulin et al. | 128/653.1 |
| 5,211,166 A | 5/1993 | Sepponen | 128/653.5 |
| 5,217,010 A | 6/1993 | Tsitlik et al. | 128/419 PG |
| 5,260,658 A | 11/1993 | Greim et al. | 324/322 |
| 5,270,485 A | 12/1993 | Jacobsen | 174/15.1 |
| 5,271,400 A | 12/1993 | Dumoulin et al. | 128/653.2 |
| 5,293,872 A | 3/1994 | Alfano et al. | 128/664 |
| 5,294,886 A | 3/1994 | Duerr | 324/318 |
| 5,307,808 A | 5/1994 | Dumoulin et al. | 128/653.2 |
| 5,307,814 A | 5/1994 | Kressel et al. | 128/653.5 |
| 5,318,025 A | 6/1994 | Dumoulin et al. | 128/653.2 |
| 5,323,778 A | 6/1994 | Kandarpa et al. | 128/653.2 |
| 5,340,010 A | 8/1994 | Torihata et al. | 228/1.1 |
| 5,347,221 A | 9/1994 | Rubinson | 324/318 |
| 5,348,010 A | 9/1994 | Schnall et al. | 128/653.2 |
| 5,352,979 A | 10/1994 | Conturo | 324/307 |
| 5,355,087 A | 10/1994 | Claiborne et al. | 324/322 |
| 5,358,515 A | 10/1994 | Hürter et al. | 607/101 |
| 5,365,928 A | 11/1994 | Rhinehart et al. | 128/653.5 |
| 5,370,644 A | 12/1994 | Langberg | 606/33 |
| 5,372,138 A | 12/1994 | Crowley et al. | 128/662.06 |
| 5,375,596 A | 12/1994 | Twiss et al. | 128/653.1 |
| 5,379,767 A * | 1/1995 | Derby et al. | 600/422 |
| 5,400,787 A | 3/1995 | Marandos | 128/653.5 |
| 5,411,476 A | 5/1995 | Abrams et al. | 604/95 |
| 5,413,104 A | 5/1995 | Buijs et al. | 128/653.5 |
| 5,419,325 A | 5/1995 | Dumoulin et al. | 128/653.2 |
| 5,421,338 A | 6/1995 | Crowley et al. | 128/662.06 |
| 5,429,132 A | 7/1995 | Guy et al. | 128/653.1 |
| 5,435,302 A | 7/1995 | Lenkinski et al. | 600/422 |
| 5,437,277 A | 8/1995 | Dumoulin et al. | 128/653.1 |
| 5,439,000 A | 8/1995 | Gunderson et al. | 128/664 |
| 5,443,066 A | 8/1995 | Dumoulin et al. | 128/653.1 |
| 5,443,489 A | 8/1995 | Ben-Haim | 607/115 |
| 5,447,156 A | 9/1995 | Dumoulin et al. | 128/653.2 |
| 5,451,232 A | 9/1995 | Rhinehart et al. | 606/192 |
| 5,451,774 A | 9/1995 | Jacobsen | 250/227.24 |
| 5,462,055 A | 10/1995 | Casey et al. | 128/653.5 |
| 5,476,095 A | 12/1995 | Schnall et al. | 128/653.2 |
| 5,498,261 A | 3/1996 | Strul | 606/29 |
| 5,507,743 A | 4/1996 | Edwards et al. | 606/41 |
| 5,512,825 A | 4/1996 | Atalar et al. | 324/309 |
| 5,520,644 A | 5/1996 | Imran | 604/95 |
| 5,524,630 A | 6/1996 | Crowley | 128/662.06 |
| 5,540,679 A | 7/1996 | Fram et al. | 606/27 |
| 5,558,093 A | 9/1996 | Pomeranz | 128/660.03 |
| 5,578,008 A | 11/1996 | Hara | 604/96 |
| 5,588,432 A | 12/1996 | Crowley | 128/660.03 |
| 5,598,097 A | 1/1997 | Scholes et al. | 324/316 |
| 5,609,606 A | 3/1997 | O'Boyle | 606/194 |
| 5,611,807 A | 3/1997 | O'Boyle | 606/169 |
| 5,623,241 A | 4/1997 | Minkoff | 335/296 |
| 5,647,361 A | 7/1997 | Damadian | 128/683.2 |
| 5,660,180 A | 8/1997 | Malinowski et al. | 128/660.03 |
| 5,682,897 A | 11/1997 | Pomeranz | 128/662.06 |
| 5,699,801 A | 12/1997 | Atalar et al. | 128/653.2 |
| 5,715,825 A | 2/1998 | Crowley | 128/602.06 |
| 5,720,287 A * | 2/1998 | Chapelon et al. | 600/439 |
| 5,728,079 A | 3/1998 | Weber et al. | 604/280 |
| 5,738,632 A | 4/1998 | Karasawa | 600/410 |
| 5,775,338 A | 7/1998 | Hastings | 128/898 |
| 5,792,055 A * | 8/1998 | McKinnon | 600/410 |
| 5,833,608 A | 11/1998 | Acker | 600/409 |
| 5,833,632 A | 11/1998 | Jacobsen et al. | 600/585 |
| 5,840,031 A | 11/1998 | Crowley | 600/440 |
| 5,868,674 A | 2/1999 | Glowinski et al. | 600/410 |
| 5,916,162 A | 6/1999 | Snelten et al. | 600/411 |
| 5,928,145 A * | 7/1999 | Ocali et al. | 600/410 |
| 5,938,609 A | 8/1999 | Pomeranz | 600/439 |
| 5,938,692 A | 8/1999 | Rudie | 607/101 |
| 5,964,705 A | 10/1999 | Truwit et al. | 600/423 |
| 5,968,052 A | 10/1999 | Sullivan, III et al. | 606/108 |
| 6,004,269 A | 12/1999 | Crowley et al. | 600/439 |
| 6,011,995 A | 1/2000 | Guglielmi et al. | 607/99 |
| 6,019,737 A | 2/2000 | Murata | 600/585 |
| 6,026,316 A | 2/2000 | Kucharczyk et al. | 600/420 |
| 6,031,375 A | 2/2000 | Atalar et al. | 324/307 |
| 6,032,078 A | 2/2000 | Rudie | 607/101 |
| 6,051,974 A | 4/2000 | Reisker et al. | 324/318 |
| 6,054,858 A * | 4/2000 | Dumoulin et al. | 324/322 |
| 6,058,323 A | 5/2000 | Lemelson | 600/408 |
| 6,061,587 A | 5/2000 | Kucharczyk et al. | 600/411 |
| 6,064,203 A | 5/2000 | Bottomley | 324/309 |
| 6,078,831 A | 6/2000 | Belef et al. | 600/424 |
| 6,104,943 A | 8/2000 | Frederick et al. | 600/410 |
| 6,171,240 B1 | 1/2001 | Young et al. | 600/410 |
| 6,171,241 B1 | 1/2001 | McVeigh et al. | 600/410 |
| 6,188,219 B1 | 2/2001 | Reeder et al. | 324/307 |
| 6,233,474 B1 | 5/2001 | Lemelson | 600/411 |
| 6,263,229 B1 | 7/2001 | Atalar et al. | 600/423 |
| 6,408,202 B1 | 6/2002 | Lima et al. | 600/423 |
| 6,549,800 B1 | 4/2003 | Atalar et al. | |
| 6,636,757 B1 * | 10/2003 | Jascob et al. | 600/424 |
| 2001/0056232 A1 | 12/2001 | Lardo et al. | 600/423 |
| 2002/0045816 A1 | 4/2002 | Atalar et al. | 600/423 |
| 2002/0097050 A1 | 7/2002 | Kellman et al. | 324/309 |
| 2002/0161421 A1 | 10/2002 | Lee et al. | 607/116 |
| 2002/0177771 A1 | 11/2002 | Guttman et al. | 600/410 |
| 2003/0028094 A1 | 2/2003 | Kumar e al. | 600/410 |
| 2003/0028095 A1 | 2/2003 | Tulley et al. | 600/422 |
| 2003/0050557 A1 | 3/2003 | Susil et al. | 600/424 |

OTHER PUBLICATIONS

Fielding, Julia R. et al., "MR Imaging of Pelvic Floor Continence Mechanisms in the Supine and Sitting Positions", AJR 171: 1607–1610 (Dec. 1998).

Perez, N. et al., "Dynamic Magnetic Resonace Imaging of the Female Pelvis: Radio–Anatomy and Pathologic Applications. Preliminary Results", Surg. Radiol. Anat. 21(2): 133–138 (1999).

Heit, M., "Intraurethral Ultrasonography: Corrleation of Urethral Anatomy with Functional Urodynamic Parameters in Stress In continent Women", Int Urogynecol Journal 11: 204–211 (2000).

Kirschner–Hermanns, R. et al., "The Contribution of Magnetic Resonance Imaging of the Pelvic Floor to the Understanding of Urinary Incontinence", British Journal of Urology 72: 715–718 (1993).

Huddleston, Harvey T. M.D. et al., "Magnetic Resonance Imaging of Defects in DeLancey's Vaginal Support Levels I, II, and III", Am. J. Obstet. Gynecol. 172: 1778–1784 (1995).

Klutke, Carl et al., "The Anatomy of Stress Incontinence: Magnetic Resonance Imaging of the Female Bladder Neck and Urethra", Journal of Urology 143: 563–566 (Mar. 1990).

Kondo, Yasushi et al., "Transvaginal Ultrasound of Urethral Sphincter at the Mid Urethra in Continent and Incontinent Women", Journal of Urology 165: 149–152 (Jan. 2001).

Strasser, Hannes M.D. et al., "Anatomy and Innervation of the Rhabdosphincter of the Male Urethra", Seminars in Urologic Oncology 18(1):2–8 (Feb. 2000).

Strasser, Hannes et al., "Transurethral Ultrasound: Evaluation of Anatomy and Function of the Rhabdosphincter of the Male Urethra", Journal of Urology 159: 100–105 (Jan. 1998).

International Search Report in PCT/US 01/10412 mailed on Mar. 5, 2002.

Atalar et al.; "High Resolution Intravascular MRI and MRS by Using a Catheter Receiver Coil"; Magnetic Resonance in Medicine, 36: 596–605, (1996).

International Search Report in PCT/US 01/03346 mailed on Nov. 5, 2001.

Lardo; "Real–Time Magnetic Resonance Imaging: Diagnostic and Interventional Applications"; Pediatric Cardiology, 21:80–98, ((2000).

International Search Report in PCT/US 01/09692 mailed on Nov. 8, 2001.

Atalar et al.; "High Resolution Intravascular MRI and MRS by Using a Catheter Receiver Coil"; Magnetic Resonance in Medicine, 36:596–605, (1996).

Partial International Search Report mailed on Nov. 01, 2001.

Kantor et al., *In vivo$^{31}$ P Nuclear Magentic Resonance Measurements in Canine Heart Using a Catheter–Coil*, Circulation Research, Aug. 1984, pp. 261–266, vol. 55, No. 2 (USA).

Merickel et al., *Identification and 3–d Quanification of Atherosclerosis using Magnetic Resonance Imaging*, Comput. Biol. Med., 1988, pp. 89–102, vol. 18, (Great Britain).

Maynor et al., *Chemical Shift Imaging of Atherosclerosis at 7.0 Tesla*, Investigative Radiology, Jan. 1989, pp. 52–60, vol. 24, No. 1.

Mohiaddin et al., *Chemical Shift Magnetic Resonance Imaging of Human Atheroma*, Br. Heart J., 1989, pp. 81–89, vol. 62 (England).

Asdente et al., *Evaluation of Atheroscleroritc Lesions Using NMR Microimaging*, Atherosclerosis, 1990, pp. 243–253 vol. 80 (Italy).

Vinitski et al., *Magnetic Resonance Chemical Shift Imaging and Spectroscopy of Atherosclerotic Plaque*, Investigative Radiology, Aug. 1991, pp. 703–714, vol. 26.

Pearlman et al., *Nuclear Magnetic Resonance Microscopy of Atheroma in Human Coronary Arteries*, Angiology, Sep. 1991, pp. 726–733, vol. 42 (USA).

Martin et al., *MR Imaging of Blood Vessel with an Intravascular Coil*, J. Magn. Reson. Imaging, 1992, pp. 421–429, vol. 2.

Waller et al., *Intravascular Ultrasound: A Histological Study of Vessel During Life*, Circulation, Jun. 1992, pp. 2305–2310, vol. 85.

Hurst et al., *Intravascular (Catheter) NMR Receiver Probe: Preliminary Design Analysis and Application to Canine Iliofemoral Imaging*, Magn. Resonance in Medicine, Apr. 1992, pp. 343–357, vol. 24.

Dumoulin et al., *Real–Time Position Monitoring of Invasive Devices Using Magnetic Resonance*, Magnetic Resonance in Medicine, Mar. 1993, pp. 411–415, vol. 29.

Koechli et al., *Catheters and Guide Wires for Use in an Echo–Planar MR Fluoroscopy System*, R. 79th Scientific Meeting, editor, Radiology, Nov. 1993, p. 319, vol. 189(P).

McDonald et al, *Performance Comparison of Several Coil Geometries for Use in Catheters* (Abstract), R. 79th Scientific Meeting, editor, Radiology, Nov. 1993, p. 319, vol. 189(P).

Merickel et al., *Noninvasive Quantitative Evaluation of Atherosclerosis Using MRI and Image Analysis*, Arteriosclerosis and Thrombosis, 1993, pp. 1180–1186, vol. 13.

Spears et al., *In Vivo Coronary Angioscopy*, Journal of the American College of Cardiology, May 1993, pp. 1311–1314, vol. 1 (USA).

Yuan et al., *Techniques for High–Resolution MR Imaging of Atherosclerotic Plaque*, J. Magnetic Resonance Imaging, 1994, pp. 43–49, vol. 4, No. 1.

Martin et al., *Intravascular MR Imaging in a Porcine Animal Model*, Magn. Resonance in Medicine, Aug. 1994, pp. 224–229, vol. 32.

* cited by examiner

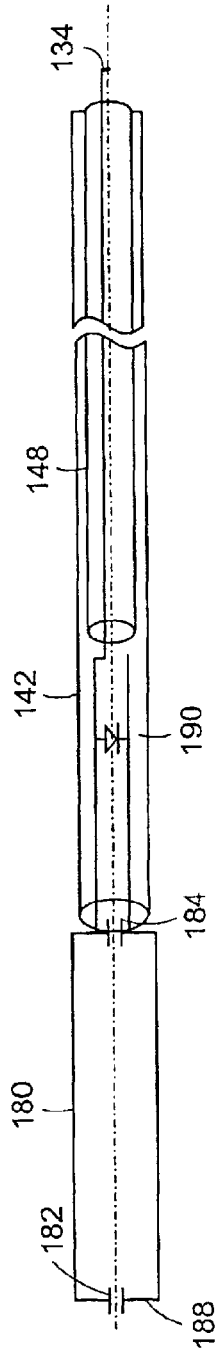
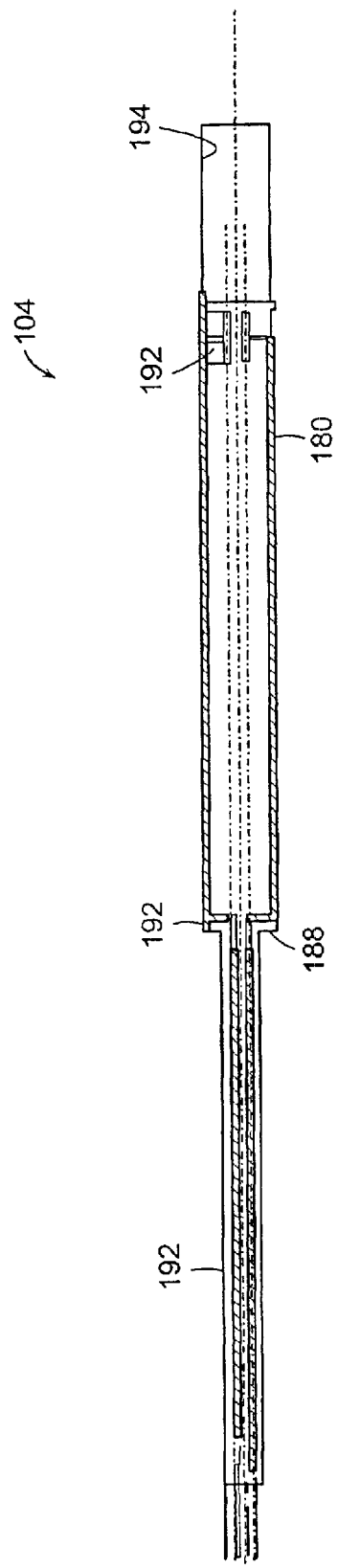

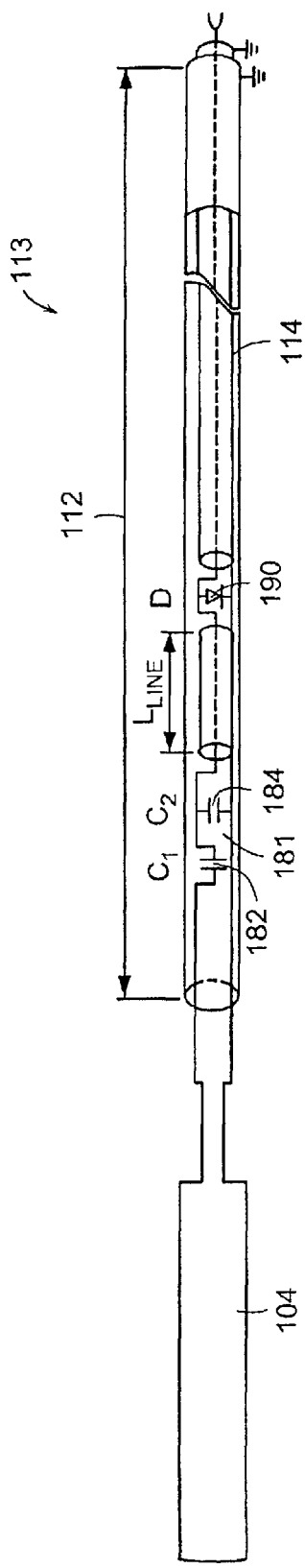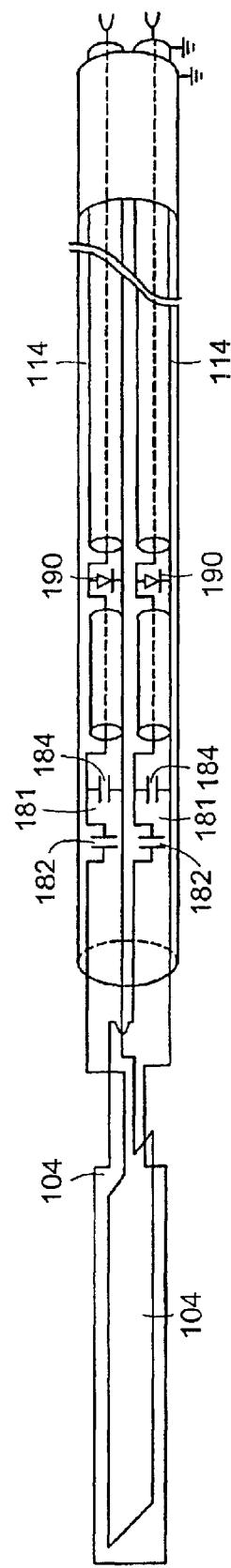
FIG. 10A
FIG. 10B

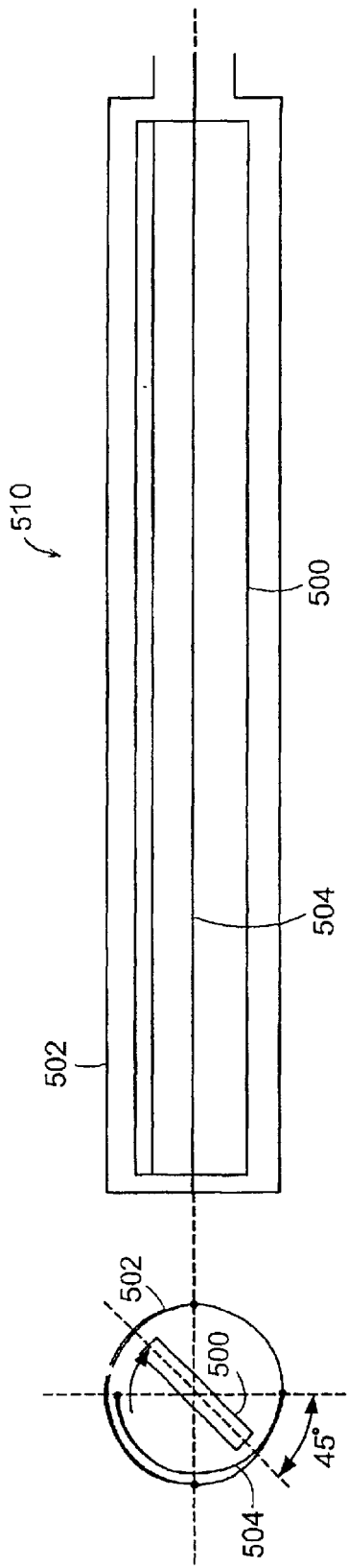
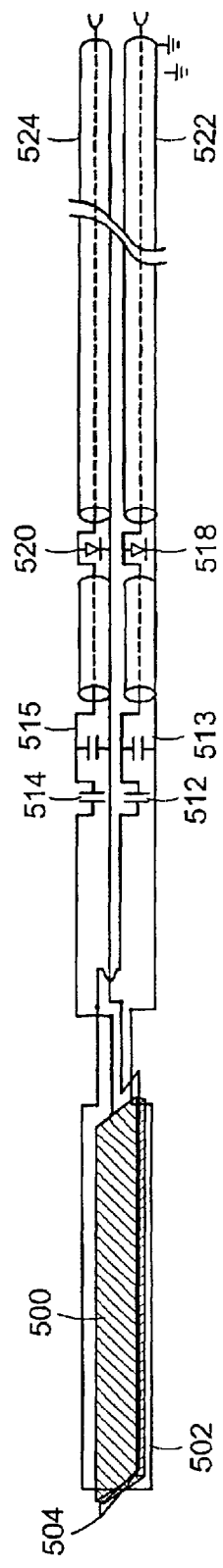
FIG. 11A
FIG. 11B
FIG. 12

A-A'

SYSTEMS AND METHODS FOR EVALUATING THE URETHRA AND THE PERIURETHRAL TISSUES

REFERENCE TO RELATED APPLICATIONS

This application claims the benefit of U.S. Provisional Patent Application No. 60/194,060 filed Mar. 31, 2000, and is a continuation-in-part of U.S. patent application Ser. No. 09/536,090 filed Mar. 24, 2000 now U.S. Pat. No. 6,675,033, and Ser. No. 09/549,921 filed Apr. 14, 2000 now U.S. Pat. No. 6,549,800, which itself is a continuation-in-part of U.S. patent application Ser. No. 09/360,144, filed Jul. 26, 1999 now abandoned, which is continuation-in-part of U.S. patent application Ser. No. 08/638,934, filed Apr. 25, 1996, now U.S. Pat. No. 5,928,145. This application is also a continuation-in-part of U.S. application Ser. No. 09/191,563 filed Nov. 13, 1998 now U.S. Pat. No. 6,263,229, and Ser. No. 09/817,893 filed Mar. 26, 2001 now U.S. Pat. No. 6,628,980. The entire disclosure of each of these applications is herein incorporated by reference.

BACKGROUND OF THE INVENTION

1. Field of the Invention

The invention relates in general to magnetic resonance imaging (MRI), and in particular to devices for in vivo MRI.

2. Related Art

Evaluation of the anatomy of the urethra and the periurethral tissues is important for the diagnosis and treatment of the number of clinical conditions in men and women. Malignant conditions include cancers of the bladder, cancers of the cervix and female genital tract, and cancers of the prostate. Non-malignant conditions may include voiding disorders such as, for example, various types of incontinences in both men and women. In addition to adult conditions, anatomic diagnosis may assist in the evaluation of pediatric anomalies of the pelvis and urinary tract.

Evaluating the anatomy of the urethra and periurethral tissues may be useful in staging bladder cancers and in determining desirable methods of treatment. Cancers of the bladder affect approximately 45,000 patients annually. Approximately 10,000 men and women die from this disease each year. Bladder tumors may be categorized as superficial non muscle-invading lesions and deep tumors with muscle invasion. Spread of the disease in more advanced stages may distort the tissues surrounding the bladder neck or urethra due to pressure from adjacent tumor or due to actual tumor invasion. Evaluation of the periurethral tissues in a bladder cancer patient may assist in identifying the stage of the disease. While endoscopic resection is suitable for superficial well-differentiated lesions, invasive tumors may require cystectomy with supravesical urinary diversion. Evaluating the degree of involvement of the bladder wall may assist the clinician with selecting the appropriate therapeutic modality.

Cancers of the female genital tract may, under certain circumstances, involve periurethral tissues. For example, in carcinoma of the cervix, spread occurs through lymphatic channels, first extending to the lymph nodes located in the tissues immediately lateral to the cervix. Direct vaginal extension may also occur. Lesions involving these tissues are designated stage two or stage three, depending on the extent of and location of tissues that are involved. Such cancers may be considered locally advanced. For locally advanced cervical cancers, radiation therapy is commonly used rather than excisional therapy. To determine the proper course of treatment, therefore, accurate anatomic information is necessary. Evaluation of periurethral pelvic tissues may provide a such useful information. Similarly, the staging of vulvar or endometrial cancers may benefit from an appraisal of the periurethral anatomy.

Adenocarcinoma of the prostate is diagnosed in about 400,000 patients annually, with approximately 45,000 patients dying from each year. The malignancy may occur in any portion of the gland, with multiple areas of involvement being present about one-third of the time. While early diagnosis is a key to survival, identifying the stage of the disease is crucial to determining proper therapy. The American System of clinical staging is divided into stages A, B, C & D. Stage A, reserved for patients who have no palpable abnormality of the prostate, is divided into A1 and A2 depending on the volume of cancer (A1<5%, A2>5%) removed by transurethral resection (TURP) for presumed benign disease. Stage B represents nodular disease palpated on rectal examination and is divided into B1 disease (nodule 1.5 cm or less) and B2 (nodule>1.5 cm). Stage C is reserved for those patients in whom disease is felt to extend outside the prostate while Stage D for those with metastatic disease. Gradually, the TNM system has gained acceptance especially since it allows for staging of those patients found to have carcinoma as a result of PSA (prostatic specific antigen) elevation and not palpable disease. Stage T1c includes those patients found to have carcinoma based on PSA elevation only, while T1a corresponds to A1, T1b to A2, T2a to B1, T2b to B2, and T3 to C.

Prostate specific antigen (PSA) levels have been correlated with the clinical extent of the disease, but evaluation of the anatomic extent of the disease contributes to determining the appropriate type of surgical intervention. Early-stage carcinoma is understood to be localized to the prostate gland without extension beyond the gland capsule and without extension to distant sites. A spectrum of treatment options exists for prostate cancer, depending on patient age, health, and tumor status. Available options include "watchful waiting", radiation therapy, radical prostatectomy, cryosurgery and hormonal ablation. Older patients (over 70 years) with small, early cancers may be candidates for watchful waiting. These patients are monitored for development of bladder outlet obstruction symptoms and distal disease. Under some circumstances, this option may also be appropriate for younger patients. Removal of the entire prostate and seminal vesicles, termed a radical prostatectomy, may be performed for organ confined disease, T1 or T2, using either a retropubic or a perineal approach. Radiation therapy provides an alternative to surgery in these patients. Radiation may be delivered either via external beam radiotherapy or via local placement of radioactive seeds within the prostate. Debate exists about the comparative efficacy of radiation therapy vs. prostatectomy. While radiation therapy may involve complications such as diarrhea, cystitis, impotence and incontinence, these last two complications are less frequently encountered with radiation than with surgery. Cryosurgical ablation is another approach to the treatment of organ-confined prostate cancer. To perform this treatment, the physician places stainless steel probes percutaneously into the substance of the prostate under ultrasound guidance. Liquid nitrogen is then circulated through the probes, creating an expanding "iceball" throughout the prostate whose extent can be monitored by using transrectal ultrasound to watch watching a freeze "front" progress within the tissue. The cycle of freezing and thawing of the prostate tissue results in coagulation necrosis of the tissue. As with other forms of therapy, patients treated with cryosurgery are at risk of developing impotence and incontinence after treatment. However, the procedure is minimally invasive and results to date have been encouraging. Advanced carcinoma, by contrast, is not appropriately treated using any of these regimens. It is therefore important to distinguish between those carcinomas confined to the gland and hence adequately treated by radical prostatectomy or other local therapies and those carcinomas extending beyond the gland which are not amenable to local cure. Because the proximal urethra is situated within the prostate gland, anatomic evaluation of tissues surrounding the urethra at the prostatic level may also serve to evaluate the prostate and its malignancies.

Of the non-malignant conditions affecting the urethra and periurethral tissues, urinary incontinence is of particular importance. At least 10 million adults in the U.S. suffer from urinary incontinence, including between 15 and 30 percent of older Americans and at least one-half of the estimated 1.5 million nursing home residents. In addition to the significant psychosocial burden borne by individuals with this ailment, incontinence involves quantifiable health care and related costs, conservatively estimated at approximately $10 billion annually. Urinary incontinence is a symptom, not a disease in itself. It occurs in several clinical patterns, each having a set of possible etiologies.

In many cases, urinary incontinence is a chronic problem, lasting indefinitely unless properly diagnosed and treated. The number of patients with urinary incontinence who have not been successfully treated remains surprisingly high. In part, this is due to inadequate knowledge about the anotomical basis, pathophysiology and potential treatments for the condition. Although new diagnostic tests have been developed, guidelines still remain to be formulated for their appropriate application. Furthermore, although a variety of therapies have been proposed, opinions differ about the best type of treatment to apply to a particular condition.

Evaluation of incontinence presently relies upon routine diagnostic tools such as history and physical examination, combined with specialized studies such as cystometrogram, electrophysiologic sphincter testing, bladder and renal ultrasound, cystourethroscopy, uroflowmetry, and videourodynamic evaluation. Ultrasound has been used transurethrally to evaluate the anatomy and function of the rhabdosphincter in the male urethra. Transvaginal ultrasound and intraurethral ultrasound have been employed in female patients also, to evaluate urinary incontinence.

The advent of intracavity magnetic resonance imaging (MRI) receiver coils for high-resolution clinical imaging of the prostate and of the uterine cervix has shown some promise as a technique for imaging the pelvic floor with increased spatial resolution compared to images acquired with the MRI body coil alone. Driven by a motivation to further increase the signal-to-noise (SNR) ratio at the region of interest, authors have reported the value of these intracavitary coils in the detailed demonstration of the female pelvic anatomy and abnormalities using a transrectal imaging approach as well as transvaginal approach for imaging. External MRI of the urethra and pelvic floor has been carried out in female volunteers and patients to elucidate the relevant regional anatomy. Endorectal and external MRI investigation has also been carried out to evaluate abnormalities of the urethral and periurethral tissues. Despite these efforts, clinical and radiological evaluation of these areas remains difficult and not completely satisfying. Although high-resolution magnetic resonance imaging with phased array pelvic, endorectal and endovaginal coils has dramatically enhanced the ability to visualize abnormalities of the female urethral and periurethral tissues, discussion and controversy still continues about the anatomy of this region.

A number of references disclose systems and methods for evaluating the anatomy of pelvic tissues including the prostate, for example U.S. Pat. Nos. 4,932,411; 5,050,607; 5,170,789; 5,307,814; 5,340,010; 5,355,087; 5,365,928; 5,451,232; 5,413,104; 5,476,095. However, there remains a need in the art for detailed and satisfactory anatomic information about the urethra and pelvic floor, especially in the female. This information would provide a significant contribution to the understanding of urinary incontinence and other urethral abnormalities in female patients, thereby contributing to an understanding of surgical approach for treatment. There further remains a need in the art for methods to provide detailed anatomic information about the male urethra and prostate in order to guide current therapeutic techniques and in order to permit the development of anatomically more refined approaches to the treatment of prostate cancer.

In addition, there is a need in the art for techniques adaptable to evaluating the anatomy of the pediatric pelvis. Genitourinary abnormalities, whether congenital or acquired, may benefit from precise anatomic diagnosis. For example, extrophy of the urinary bladder is part of a spectrum of anatomic deformities which result from lack of ingrowth of the abdominal mesoderm into the cloacal membrane, an embryologic structure which is part of the infraumbilical covering of the developing abdominal wall. In its complete form the bladder mucosa is exposed on the anterior abdominal wall, the pubic symphysis has not fused and the urethra is epispadic. A lesser degree of the same complex includes epispadius alone. Cloacal extrophy is an extremely rare congenital anomaly in which there are two extrophied hemibladders separated by a bulging cecum and ileal orifice. Correction of the anatomic abnormalities with restoration of normal bladder function and urinary continence as well as normal penile appearance in the male is the goal of treatment. Repair of cloacal extrophy is challenging for it requires staged reconstruction of the pelvic urinary structures as well as the gastrointestinal tract. A more thorough understanding of the complex pelvic and urological anatomy may assist surgeons in planning and executing the necessary reconstructive procedures.

It is understood that diagnostic techniques may be combined with therapeutic techniques for pelvic conditions. A better understanding of regional and local anatomy and an appreciation of the relevant pathology may facilitate accurate and effective treatment. There remains a need in the art for diagnostic techniques that are combinable with therapeutic modalities useful for malignant and nonmalignant conditions in the pelvic region.

Techniques of magnetic resonance imaging (MRI) or magnetic resonance spectroscopy (MRS), specialized radiofrequency (RF) may be applicable to these diagnostic and therapeutic problems. RF receiver coils may be placed at the region of interest to increase the signal-to-noise ratio (SNR) for better image (spectrum) quality in MRI or MRS. RF Receiver coils can broadly be separated into categories of volume coils, surface coils and endoluminal coils. Volume coils contain the region of interest within their volume and the imaging region is directed toward the inside of the coil. Surface coils are placed on top of the region of interest and their imaging region is directed to either side of the coil. Endoluminal coils are inserted into natural (urethra, prostate, vagina, rectum, oesophagus, pancreas, etc.) or artificial (endovascular, etc.) orifices of the human or animal body. Their imaging region is directed towards the outside of the coil to provide high-resolution imaging (spectra) of the region surrounding the coil. Different coil designs for a potential endoluminal application are available in the art. The endoluminal RF coils designs exist in multiple forms, including: rigid (GE prostate biopsy guidance coil, (R. D. Watkins, K. W. Rohling, E. E. Uzgiris, C. L. Dumoulin, R. D. Darrow and R. O. Giaquinto, "*Magnetic Resonance Image Guided Biopsy in Prostate*", page 412, Book of Abstracts, ISMRM 2000), flexible (Atalar, E., P. A. Bottomley, and E. A. Zerhouni, Method of Internal Magnetic Resonance Imaging and Spectroscopic Analysis and Associated Apparatus, Assignee: Johns Hopkins University: U.S. Pat. No. 5,699,801, Dec. 23, 1997), and others. A quadrature/phased array endo-luminal design was also disclosed earlier (Atalar, U.S. Pat. No. 5,699,801).

However, there remains a need for providing high SNR and increased signal homogeneity in endocavitary designs. Mutual inductance between two or more independent but geometrically adjacent coils, tuned to the same resonance frequency may under certain circumstances improve the SNR and signal homogeneity, but such designs can also result in coupling between the coils that might result in poor signal performance and decreased signal penetration depth into the tissue. Usually, this mutual inductance is compensated for by adding combinations of capacitors, inductors, and/or other electronic elements to the resonant circuit of the coils. Another means of compensation is, to mechanically align the two or more coils in a way to each other, so that the coils are geometrically isolated from another.

Geometric decoupling, however, does not always result in sufficient isolation. The overall coil performance might be still degraded due to residual coupling between the coils. However, there has been no simple method of eliminating coupling between elements of these types of designs taught, thereby impeding the clinical uses of such devices. The use of a metallic paddle to steer the magnetic flux of a coil as a means to insulate two or more adjacent coils from each other was published in the literature in 1946 by Bloch, Hansen and Packard (F. Bloch, W. W. Hansen, M. E. Packard, *Phys. Rev.* 70:474 (1946)) and was then reconsidered by Andrew (E. R. Andrew, Nuclear Magnetic Resonance. Pp.56–63, Cambridge Univ. Press, London, (1955)) and then by Hoult et al. (D. I. Hoult, C. N. Chen, V. J. Sank, Quadrature detection in the laboratory frame. *Magn. Reson. Med.* 1, 339–353 (1984)). In these publications, however, a rather small paddle was used to decouple large volume coils from one another, to minimize distortions of the $B_1$ field homogeneity to the inside of the coil. The application of such a paddle to an 'inside out' design of endoluminal coils, as first described in this report, enabled the paddle to be inserted into the most sensitive region between the coils. Furthermore, the paddle could be designed larger relative to the size of the coils, providing a very effective means of coil insulation, virtually without affecting the $B_1$ field toward the outside of the coil. No additional electronics were required to achieve an isolation of about 50 dB. Signal homogeneity as well as signal penetration depth and therefore image quality was markedly improved by minimizing the mutual inductance between the coils. There remains a need in the art, therefore for a means to minimize the mutual indictance between two or more independent RF transmit or receive coils in MRI or MRS that is simple to implement and effective. There is a further need to device a RF coil for endoluminal applications that can improve signal homogeneity and signal penetration depth.

SUMMARY OF INVENTION

In one aspect, the present invention provides an apparatus for magnetic resonance imaging of an anatomic region of a human pelvis. In one embodiment, and apparatus according to the present invention may provide an endourethral magnetic resonance imaging coil comprising an antenna, and interface circuit interposed between the antenna and a MRI machine, said interface circuit being in electrical communication with the antenna and being in electrical communication to the MRI machine and comprising a tuning-matching circuit, a decoupling circuit and a balun circuit, and a housing enveloping the antenna. The antenna may be formed on a flexible circuit. The interface circuit may be enclosed within an interface box connected to the antenna by a connector. The antenna may be a receive-only coil. The tuning-matching circuit may comprise at least two sets of capacitors, a first set in series and a second set in parallel. The decoupling circuit may comprise a PIN diode. The interface circuit may further comprise a DC regulating circuit. The housing may be sealed at a distal end. In this embodiment and in all embodiments of the present invention, the electrical communication between the interface circuit and the MRI machine may be made using a wireless connection, and in certain other embodiments of the present invention, the electrical communication between the interface circuit and the antenna may be made using a wireless connection.

In another aspect, the invention provides an apparatus for magnetic resonance imaging (MRI) of an anatomic region of a human pelvis, comprising an endourethral magnetic resonance imaging coil system, comprising a first antenna and a second antenna, wherein said second antenna is oriented at a preselected position with respect to said first antenna; and further comprising an interface system interposed between a MRI machine and said first and second antennas, said interface system being in electrical communication with said MRI machine and with each of said first antenna and said second antenna, said interface system comprising a tuning-matching system, a decoupling system and a balun system; and further comprising a housing enveloping at least one of said first antenna and said second antenna.

In yet another aspect, the present invention provides a system for treating an anatomic region within a pelvis of a patient, comprising an elongate member insertable into a urethra of the patient and temporarily retainable in said urethra, said elongate member housing an endourethral imaging system and an endourethral therapeutic system, wherein said endourethral imaging system comprises an endourethral MRI coil comprising an antenna, and said endourethral therapeutic system comprises an endourethral delivery device to deliver a mode of therapy transurethrally to an area of the anatomic region imaged by the endourethral imaging system; and further comprising an interface circuit interposed between said antenna and a MRI machine, said interface circuit being electrical communication with said antenna and being in electrical communication with the MRI machine, said interface circuit comprising a tuning-matching circuit, a decoupling circuit and a balun circuit.

In one aspect, the present invention may provide methods for treating an anatomic region within a pelvis of a patient. In one practice of the method, steps include providing a medical device comprising an elongate member insertable into and temporarily retainable within a urethra of the patient, said elongate member housing an endourethral imaging system and an endourethral therapeutic system, wherein said endourethral imaging system comprises an endourethral MRI coil comprising an antenna, and said endourethral therapeutic system comprises an endourethral delivery device to deliver a mode of therapy transurethrally to an area of the anatomic region imaged by the endourethral imaging system; providing an interface circuit interposed between said antenna and a MRI machine, said interface circuit being in electrical communication with said antenna and being in electrical communication with the MRI machine, said interface circuit comprising a tuning-matching circuit, a decoupling circuit and a balun circuit; providing the MRI machine; inserting said elongate member into the urethra of said patient; temporarily retaining said elongate member in said urethra; positioning the pelvis of the patient in a diagnostically effective position relative to the MRI machine; using the MRI machine to excite magnetic resonance signals within tissues surrounding the anatomic region; applying gradient magnetic pulses to said human pelvis to spatially encode the magnetic resonance signals; receiving said magnetic resonance signals in said endourethral MRI coil and producing responsive output signals therefrom; processing said output signals to obtain an image of the anatomic region; identifying an area of the anatomic region to be treated; positioning the endourethral therapeutic system in therapeutic proximity to the area; and delivering transurethrally the mode of therapy to said area using said transurethral delivery device. As used herein, temporarily retaining the elongate member in the urethra refers to any temporary retention, no matter how long or short in duration, which is adequate to accomplish some aspect of the diagnostic or therapeutic procedures of the method. Temporary retention permits the elongate member to be repositioned in a different position during the course of diagnosis or treatment. Positioning the pelvis of the patient in a diagnostically effective position will be understood to practitioners of the MRI art to relate to the proper positioning of the body part to be imaged with respect to the main MRI machine. Positioning the endourethral therapeutic system in therapeutic proximity to the area will be understood by practitioners in the art to refer to any positioning from whence the endourethral therapeutic system may deliver a therapeutically effective amount of the mode of therapy to the area of the anatomic region to be treated.

In another aspect, the present invention may provide methods of evaluating an anatomic region of the human pelvis. In one practice, the method may comprise providing an endourethral MR receiver coil having an antenna disposed upon a flexible circuit, providing an interface circuit in electrical communication with said antenna, said interface circuit comprising a tuning-matching circuit, a decoupling circuit, and a balun circuit, providing a housing enveloping the antenna, providing an MRI machine in electrical communication with the interface circuit, inserting the endourethral MR receiver coil into a human urethra within the human pelvis, situating the human pelvis within a main magnetic field of the MRI machine, imposing the main magnetic field on the human pelvis, applying RF pulses to the human pelvis to excite magnetic resonance signals within the human pelvis, applying gradient magnetic pulses to the human pelvis to spatially encode the magnetic resonance signals received resonance signals in the endo urethral MR receiver coil, emitting responsive output signals from the endourethral MRI receiver coil, processing the output signals and converting them to information about the anatomic region of the human pelvis, thereby to evaluate the anatomic region.

The systems and methods of the present invention may be directed to a male or to a female subject. In one aspect, these systems and methods may be directed towards the diagnosis of an abnormality of the prostate. In another aspect, these systems and methods may be directed towards the diagnosis of an abnormality of the female pelvic floor. Coils designed for the male or the female urethra may include specific features adaptable to male or female regional anatomy. Two different coil designs for intraurethral positioning may be included as embodiments of the present invention: a) single-loop coil, and b) quadrature coil. A balun circuit may be implemented into the design of both coils to reduce potential RF heating effects and to improve coil performance. An image intensity correction (IIC) algorithm may be used to compensate for the $B_1$ signal variation of the endoluminal coils across the small field of views (FOV's) being used.

BRIEF DESCRIPTION OF THE FIGURES

The following figures depict certain illustrative embodiments of the invention in which like reference numerals refer to like elements. These depicted embodiments are to be understood as illustrative of the invention and not limiting in any way.

FIG. 6 provides an electrical schematic of an embodiment of an imaging coil and interface circuit.

FIG. 7 provides a schematic view of an imaging coil embodiment.

FIGS. 10A and B provide schematic electrical diagrams of a single imaging coil and interface circuit and a double imaging coil and interface circuit.

FIGS. 11A and B provide a schematic longitudinal and cross-sectional view of two imaging coils combined with a decoupling paddle.

FIG. 12 provides a schematic electrical diagram of two imaging coils and interface circuits combined with a decoupling paddle.

DETAILED DESCRIPTION OF THE INVENTION

1. General

Figure 1:
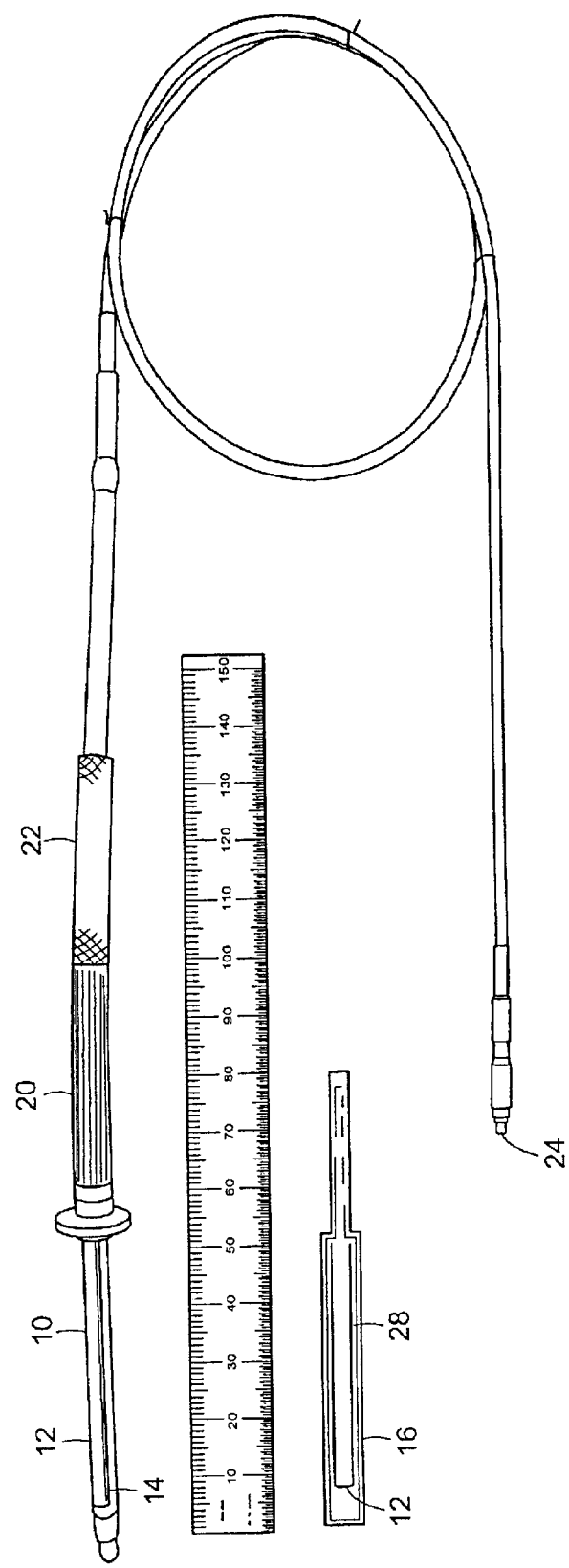
FIG. 1 provides a perspective view of an embodiment of an endourethral imaging system according to the present invention.

Without being bound by theory, certain of the following anatomical structures may be amenable to evaluation using the systems and methods of the present invention. The female urinary bladder and urethra are situated on the intrapelvic surface of the anterior vaginal wall, anchored to the distal vagina by the urogenital diaphragm and to the proximal vagina vesicocervicouterine junction. The anterior surface of the proximal urethra is firmly anchored to the posterior aspect of the symphysis pubis by the pubourethral ligaments, and to the remaining distal vagina by the lower two-thirds of the urogenital diaphragm. The lateral bladder wall is supported by the anterior vaginal wall attachments to the pelvic side wall. Vaginal detachment from the lateral pelvic side wall can result in prolapse, with accompanying secondary posterior bladder dissent. Weakness or injury to the levator ani muscles may contribute to laxity or detachment of the vaginal wall and the development of stress incontinence. The anterior vaginal wall is firmly fixed by pubococcygeus muscle fibers inserting on the vaginal wall and by the cardinal and uterosacral ligaments.

The male and the female urethral suspensory mechanisms are analogous. The male urethra extends from the internal urethral orifice of the urinary bladder to the external urethral orifice at the end of the penis. It is divided into three portions, the prostatic, the membranous, and the cavernous urethra. The prostatic portion of the urethra is the widest part, running almost vertically through the prostate from its base to its apex and lying nearer to the anterior aspect of the prostate. At this level, the urethra is surrounded by the prostate gland. The membranous portion of the urethra is the shortest section, extending downward between the apex of the prostate to perforate the urogenital diaphragm about 2.5 cm below and behind the pubic symphysis. The membranous portion is completely surrounded by sphincteric fibers. More recently, anatomists have described the rhabdosphincter of the male urethra, a structure thought to be either part of the urogenital diaphragm extending to the prostate or a striated muscle extending from the base of the bladder to the urogenital diaphragm. More recent studies have identified this structure as vertically extending from the bulb of the penis to the region of the bladder neck along the prostate and membranous urethra to form a horseshoe shape loop around the anterior and lateral aspects of the membranous urethra and to insert dorsally in the perineal body by way of a broad tendinous raphe. The cavernous portion of the urethra is contained in the corpus cavernosum, extending from the end of the membranous portion to the external urethral orifice. As in the female, the male urethral suspensory mechanism is traditionally understood to be composed of 3 continuous structures: the anterior pubourethral ligament, the intermediate pubourethral ligament, and the puboprostatic or posterior pubourethral ligament. The bilateral urethral suspensory mechanism inserts along the lateral border of the urethra to form a supporting sling from the pubic arch. The lateral surfaces of the levator ani muscle are oriented vertically in the pelvis and applied directly to the entire lateral surface of the prostate. The bladder is primarily oriented anteriorly to the prostate. In cross-section, the trigone of the bladder and the anterior fibromuscular stroma of the prostate appear as a single unit in continuity. Pubovesical ligaments attach the bladder and prostate to the pubis.

Urinary continence depends on urine being stored in a receptive bladder closed by a competent sphincter mechanism. Incontinence may result from a storage problem (detrusor instability) or from a problem with the sphincter mechanism. The sphincter mechanism includes the activity of the internal sphincter, the periurethral support to the proximal urethra, and the function of the external sphincter. In addition, a complex neurologic system coordinates urethral and bladder function to permit either urinary storage or urinary voiding, depending on social requirements. A number of factors may adversely affect the continence mechanism. Surgical trauma, such as may occur with a radical prostatectomy, may injure the sphincter mechanism. The neuromuscular damage to the pelvic floor that occurs with childbirth may affect the structures supporting the urethra and maintaining the normal female urethrovesical angle. Lack of estrogen with menopause is also understood to affect the tone of the pelvic and periurethral tissues. Understanding of the anatomic etiology of any incontinence disorder is central to determining proper treatment.

Clinical forms of urinary incontinence in adults include stress incontinence, urge incontinence, overflow incontinence, and a mixed form. Choice of appropriate therapy depends upon clinical diagnosis and understanding of the underlying anatomic abnormality. In stress incontinence, dysfunction of the bladder outlet leads to leakage of urine as intra-abdominal pressure is raised above urethral resistance during coughing, bending, laughing, or lifting heavy objects. Stress incontinence has many causes, including direct anatomic damage to the urethral sphincter and weakening of the bladder neck supports. Urge incontinence involves a patients sensing the urge to void without the ability to inhibit voiding long enough to reach the toilet. In many cases, uninhibited bladder contractions contribute to the incontinence. Among the causes of this condition are central or peripheral neurologic abnormalities and local irritating factors. Overflow incontinence occurs when the bladder is unable to empty normally and thus becomes overdistended, leading to frequent small-volume urine loss. Causes include neurological abnormalities and any systemic or local factor that obstructs outflow. Many cases of urinary incontinence have mixed etiologies, incorporating aspects of more than one subtype.

Stress incontinence may reflect weakness in the pelvic floor, particularly in females. The pelvic floor is understood to comprise three compartments: anterior, posterior and middle. Weakness in the anterior compartment may lead to urological consequences. Weakness of the medial and posterior pelvic floor may lead to prolapse, either vaginal or rectal. Anatomic defects of the interior, middle or posterior zones may result in voiding or other dysfunction. An external muscular mechanism exists to open the vagina and closes the urethral outflow tract. The same pelvic floor muscles permit the exertion of control over urination. The stretched vagina prevents the filling bladder from activating stretch receptors in the bladder neck. Laxity in the vaginal or perivaginal tissues may interfere with the transmission of these muscle forces, thereby interfering with the opening and closing of the urethra. Such laxities may also interfere with the neurologic processes of peripheral control so that the bladder is instructed to swing between open and closed modes in an unstable pattern. Tissue laxity may in this way cause premature activation of the micturition reflex with resulting detrusor instability, or may result in stress incontinence or other abnormal emptying patterns. A number of muscle functions impact the opening and closing of the proximal urethra and bladder neck, including the pubourethrovesical ligaments, the suburethral vaginal wall, the pubococcygeus muscles and the levator plate. The connective tissue surrounding these muscular tendinous units permits the transmission of forces from the muscles to the urethra, thereby preserving volitional continence.

Men experience urinary continence less than women because of the differences male and female pelvic anatomy. In men, there is a predominance of overflow incontinence and detrusor instability problems. Stress incontinence in men is seen almost exclusively following prostate surgery. For some prostate induced urinary incontinence, biofeedback can be an effective treatment. Nearly continuous urinary leakage following prostate surgery may require the implantation of an artificial sphincter. Despite improvements in the anatomic understanding of the prostate region and despite refinements in surgical technique, a significant number of patients still experience incontinence after radical prostatectomy. This may be due to damage to sphincter structures, to bladder dysfunction, to an obstructive stricture, or to some combination of these. A thorough anatomic evaluation of the urethra and periurethral structures is essential to determining the cause of such incontinence, and hence to selecting an appropriate type of treatment.

Evaluation of the urethra in female and male patients presents challenging clinical and radiological problems. The ability to image the urethra in higher resolution than currently clinically available may permit more satisfactory investigation of incontinence and other urethral abnormalities. Contributing to the investigation of the female urethra, the development of MR receive coils for the novel intraurethral approach provided by the present invention may enable the acquisition of ultra-high resolution MR images of the female urethra with a spatial in-plane resolution down to 78×78 $\mu$m, acquired within 8:32 min. Further, the systems and methods disclosed herein may permit more accurate evaluation of the male prostate through MR receive coils inserted transurethrally. Elements useful in the design of an intraurethral RF receive coil for the female urethra include: a) small device diameter to fit the lumen of the urethra, b) longitudinal signal coverage of the length of the urethra, c) minimized radial sensitivity falloff to the coil to improve the penetration depth, d) homogeneous response to radially equidistant objects, and e) homogeneous response to axially equidistant objects. Similar characteristics pertain in the male urethra, though the longitudinal signal coverage may be directed at a more circumscribed region, that of the prostatic urethra. For use in male patients, the device advantageously is sufficiently flexible to be advanced atraumatically to the appropriate intraurethral level. Additionally, the safety of the device has to be considered when a potential human use is envisioned. An important safety concern associated with the incorporation of an RF antenna into the human body is the possibility of localized RF heating caused by the coil or the coaxial cable connecting the coil to the scanner. While the small-area loop coils in this investigation are not considered to pose a high risk in terms of RF heating, the overall design with a coaxial cable connecting the coil to the scanner, potentially can pick up RF energy which could lead to tissue heating at the distal end of the coil.

2. System Adapted for Visualization of the Female Urethra

FIG. 1 depicts an embodiment of the present invention adapted for use in the female urethra. In the depicted embodiment, the outer diameter of the intraluminal coil 10 is desirably limited to 15 F (5 mm). In this embodiment, the coil 10 has a length of 50 mm. Thus, the whole length of the adult urethra, which is, in the range of 32–40 mm, can be covered with highest sensitivity and homogeneity of the coil 10. In the depicted embodiment, the imaging loop 12 is housed in a biocompatible polymeric tubing 14 with 5.0 min outer diameter (OD) and 4 mm inner diameter (ID). The imaging loop 12, which is formed upon a flexible circuit 16 may in certain embodiments be mounted onto another tubing or resilient stiffener that adds support to the flexible circuit 16 preventing it from collapsing or kinking during use. The distal end of the polymeric tubing 14 may be sealed to isolate the coil 10 from direct contact with physiological tissue and fluids. Alternatively, the imaging loop 10 may be covered by an insulator directly applied to it which similarly serves to isolate the coil 10 from direct contact with physiological tissue and fluids. During typical clinical use in the female urethra, the distal 5–6 cm of the coil may be inserted in the urethra, while the coil electronics mounted on the proximal end of the flexible circuit 20 and cable system 22 will stay out of the body. A stopper may prevent the coil from being inserted further into the urethra. The proximal end of the cable system 22 is operatively connected to a connector 24 such as a BNC or its equivalent, permitting attachment of the intraluminal coil system 10 to a MRI machine.

While the depicted embodiment shows a housing formed from a biocompatible polymeric tubing 14, it is understood that a variety of materials may be used to form the outer layers housing the imaging loop systems of the present invention. As will be appreciated by practitioners in the relevant arts, flexible materials such as silicone, polyurethane, or other low durometer substances can be used to form the housing surrounding the imaging loop systems. Furthermore, the housing may be formed with specific tips or incorporate specific urological designs as appropriate. For example, a Coudé catheter tip may be provided, or a coiled tip adapted for passage through tortuous passages, or the housing may be modified to accommodate use of filiforms and followers or other urological tools. Other modifications will be apparent to practitioners of ordinary skill that will facilitate passage of the inventive apparatus into and through the passageways of the male, female and pediatric pelvis, including the urinary tract and the urethra.

Two different kinds of coils may be built with the same outer dimensions: a single loop as shown in this figure, and a quadrature coil, illustrated in FIG. 10B. The single-loop urethra coil as shown in this figure design may be based on a loop circuit, which consists of a copper trace etched on a flexible circuit 16, as shown in the inset of FIG. 1. In an exemplary embodiment, the copper trace may coated with a polyamide layer to prevent oxidation during the sterilization process and to maintain the integrity of the copper trace during use. Other types of coating for the copper trace will readily be envisioned by practitioners of ordinary skill in the art. The flexible circuit 16 as shown in this figure enables the overall coil design to be semi-flexible and to give reproducible results in manufacturing. In one embodiment, the separation of the conductors 28 on the flexible circuit 16 in its final assembly may be 4 mm. Tuning and matching capacitors may be soldered directly onto the surface of the proximal end of the circuit 20, as described in more detail below.

Figure 2:
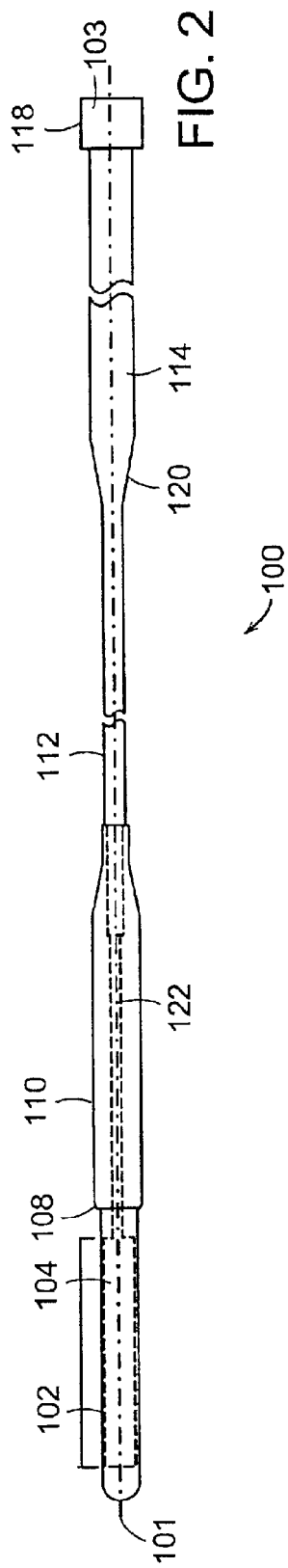
FIG. 2 provides a schematic view of an embodiment of an endourethral imaging system adapted for use in a female urethra.

FIG. 2 provides a schematic view of an embodiment of an imaging system 100 according to the present invention. As shown in FIG. 2, an imaging loop coil 104 may be deployed within a polyurethane tubing 102 that provides a housing for the imaging loop 104. The distal end 101 of the polyurethane tubing 102 may be sealed to protect the imaging loop coil 104 from contact with body fluids. The imaging loop 104 may be formed on a circuit, as will be described in more detail below. A layer of polyurethane tubing 110 extends proximally to cover the braiding (not shown) that shields the tuning-matching and decoupling circuits that form part of the interface circuit connecting the imaging loop 104 with the cable system that may be attached to the MRI machine (not shown). This figure also shows a balun 112, here depicted as an assembly of coaxial cable approximately 87 cm long. It is understood that a balun circuit may be used to prevent unbalanced shield currents from establishing resonance on the coil, thereby to reduce heating effects. In the depicted embodiment, the balun circuit may also be used to shield the tuning-matching and decoupling circuits that form part of the interface circuit, in order to reduce signal inhomogeneities generated by the entire assembly and changes in loading conditions. Proximal to the balun 112 is a coaxial cable 114, with the junction between them shown is the coax-triax junction 120. The coaxial cable 114 extends proximally for a distance of about 50 cm in the depicted embodiment. Affixed to the proximal end 103 of the coaxial cable 114 is a connector 1/8 such as a BNC connector which permits attachment of the imaging system 100 to the MRI machine (not shown). During clinical use, the distal 5 to 7 cm of the imaging coil 104 may be inserted into the female urethra. The rest of the imaging system 100 remains outside the body. The dimensions provided in this figure are meant to be illustrative only. It is understood that other dimensions and diameters may be adapted to different anatomic conditions. For example, the size and shape of the pediatric female urethra will require modification of the aforesaid dimensions, as will be apparent to practitioners of ordinary skill in the art.

Figure 3:
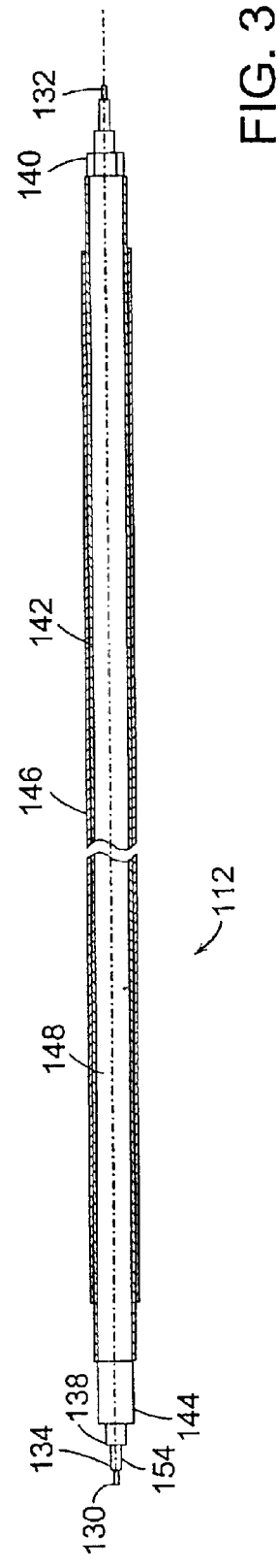
FIG. 3 depicts a schematic of a triaxial cable assembly.

FIG. 3 shows in more detail the triaxial cable assembly that is used to provide a balun for an embodiment of an imaging system according to the present invention. This figure shows a balun 112 in cross-section with its layers revealed. At the distal end 130 of the depicted segment of an imaging system according to the present invention, the core conductor 134 is shown to be centrally positioned within the layers of the cable assembly. This core conductor 134 is connected to the conductor traces in the flexible circuit (not shown), as will be described in more detail below. Surrounding this core connector 134 is a layer of primary insulation 154, surrounded by a layer of primary shielding 138, available to be soldered to the flexible circuit (not shown). Surrounding the primary shielding 138 is a layer of secondary insulation 144. Proximal to the flexible circuit assembly (not shown) is a standard coaxial cable 148. This structure provides a layer of secondary shielding/braiding 142 covering the secondary insulation 144, and it is in turn surrounded by an external insulation layer 146, which may be formed from PET or similar material. At the proximal end 132 of the depicted segment, connection to a micro-coax connector or to a RG 58 coaxial cable may be arranged. The secondary shielding 142 may be soldered to the primary shielding 138 at a solder point 140.

Figure 4:
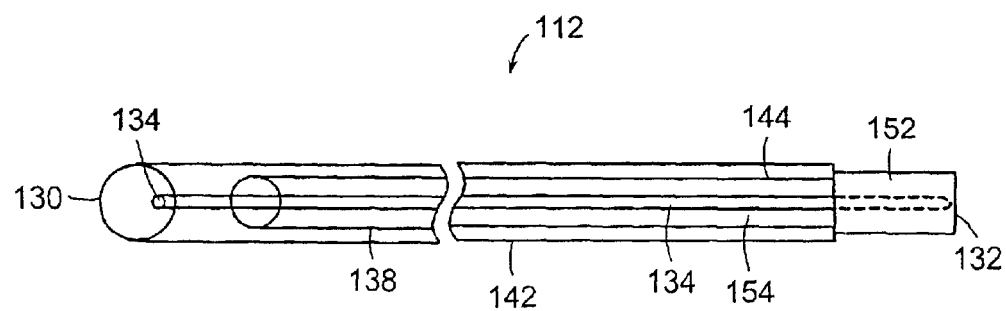
FIG. 4 provides a schematic diagram of a balun assembly.

FIG. 4 provides a schematic diagram of a balun assembly 112 according to an embodiment of the present invention. As previously described, at the distal end 130 of the depicted segment the core conductor 134 is revealed, this structure to be connected to the conductor traces on the flexible circuit of the imaging coil (not shown). Surrounding the conductor 134 is a layer of primary insulation 154. External to this is a layer of primary shielding 138 of the coaxial cable. External to the primary shielding 138 is a layer of secondary insulation 144. External to the secondary insulation 144 is a layer of external braiding 142 that acts as the secondary shielding. At the proximal end 132 of the depicted segment, a micro BNC connector 152 may be applied that attaches the primary shielding 138 and the secondary shielding 142 to the ground of the connector 152. This triaxial cable may be custom-made by inserting a micro coaxial cable in a tubular silver plated copper braid. In one embodiment, a polyester heat shrink tubing may then be drawn over the entire assembly.

Figure 5:
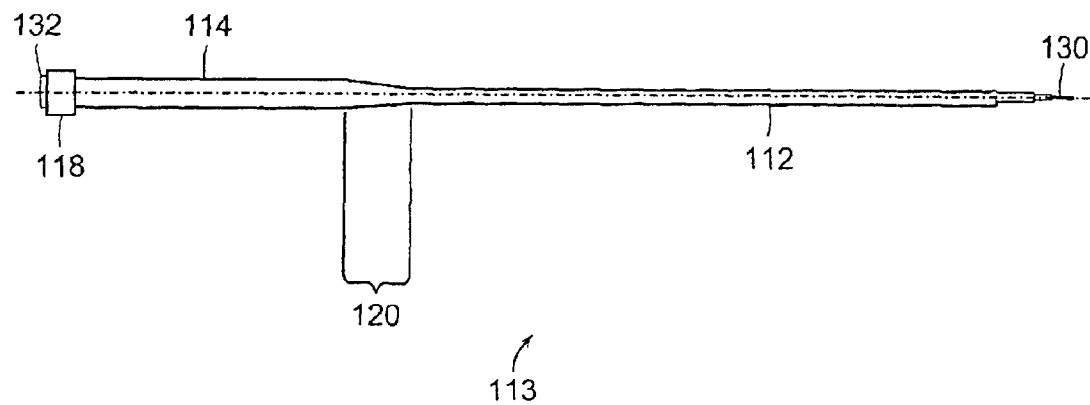
FIG. 5 provides a schematic diagram of a cable assembly.

FIG. 5 depicts an embodiment of a cable assembly 113 connectable to an imaging coil (not shown) according to the present invention. The cable assembly 113 depicted in this figure comprises a balun assembly 112, a stripped distal end 130 connectable to a flexible circuit imaging coil (not shown), a coaxial cable 114 situated proximally, a proximal connector 118 such as a BNC connector located at the proximal end 132, and a solder joint or transition section 120 between the balun assembly 112 in the coaxial cable 114. Illustrative dimensions are provided. An extension cable 114 such as a 50 cm RG 58 coaxial cable terminated with a male BNC connector 118 at the proximal end may facilitate connection to the MRI scanner's surface coil port.

FIG. 6 provides an electrical schematic of an embodiment of an imaging coil 104 and an interface circuit comprising a balun, a tuning-matching circuit and a decoupling circuits. The tuning-matching circuit comprises two sets of capacitors, one set 182 in series and the other set 184 in parallel, mounted respectively on the distal and proximal end of the flexible circuit to adjust the output of the imaging loop 180 to 50 ohm impedance. The pads for these capacitors may be etched on the flexible circuit. The value of the individual capacitors may be determined for each coil. The coils may be tuned to 63.86 MHz and matched to 50 Ohms while inserted into a 4.5 liter polyethylene container (150× 150×200 mm) filled with 0.9% NaCl-solution to approximate the loading conditions of a coil inserted into a patient. SNR performance and signal homogeneity tests may be performed with the coil inserted in this phantom. In one embodiment, the value for the parallel capacitor 184 may be about 382 pF, and about 76 pF for the series capacitors 182. In another embodiment, the value of the capacitors may be 300 pF for the parallel capacitor and 95 pF for the series capacitors respectively. Nonmagnetic "case A-size" high quality ceramic chip capacitors may be employed (American Technical Ceramics ATC, Huntington Station, N.Y.), although other alternatives will be apparent to skilled practitioners. A nonmagnetic small diameter 50 Ohms coaxial cable with 1.2 mm OD (K 01152-07, Huber & Suhner, Herisau, Switzerland) may be employed to conduct the signal from the tuning/matching electronics to the surface coil port of the scanner.

The tuning-matching circuit gets input from the imaging coil 104. The output from the tuning-matching circuit is transmitted to the preamplifier (not shown) of the MRI machine through a decoupling circuits and a balun circuit. The decoupling circuit is formed from a PIN diode 190, also located on the flexible circuit. The decoupling circuit is used to detune the coil during transmission by the body coil and ground the DC currents introduced by the scanner during scanning sequence. To decouple from the body coil during transmission, an active decoupling network is implemented to avoid RF concentrations at the coil conductors. In one embodiment, the decoupling circuit is built into the same flexible circuit as the imaging coil 104 and the tuning-matching circuit. Decoupling from the body coil may be achieved in one embodiment by placing a PIN diode 190 in the circuit at a distance of 1.5 cm proximal to the parallel capacitors 184. To detune the endoluminal receive coil during transmission with the scanner body coil, an active decoupling network may be implemented to avoid RF field concentrations at the coil conductors. In one embodiment, this was achieved by placing a PIN diode (Type 7204) in parallel with the tuning/matching capacitor 184 between the central conductor and the ground of the coaxial cable. In this embodiment, the PIN diode 190 was placed in the coaxial cable at a critical distance l=70 min away from the capacitor 184. Thus the inductance $L_{line}$ of the coaxial cable and the capacitance of the capacitor 184 establish a resonant circuit at the operating frequency ω0, (ω0,=63.87 MHz in certain embodiments) when the diode is switched on. During transmission of RF pulses with the body coil, a triggered direct current (DC) voltage at the scanner surface coil port actively switches on the PIN diode 190. The impedance seen by the receive coil becomes high and detunes this coil during transmission. During receive mode, the diode 190 is opened by an inverse DC voltage provided by the scanner, setting the endoluminal receive coil back to resonance. During the receive mode, the inverse DC voltage provided by the preamplifier switches off the diode in the coil is set back to resonance at the operating frequency ω0, (ω0,=63.9 MHz in certain embodiments).

As previously described, the balun circuit comprises an assembly of coaxial cable 148 87 cm long with additional shielding 142 over the entire assembly, with the secondary shielding 142 being electrically connected to the primary shielding (not shown) at the proximal end of the imaging system. The secondary shielding 142 or the braiding is extended to shield the tuning matching capacitors and the PIN diode. The total length of the balun circuit may be about 86.5 cm. This length corresponds to quarter wavelength, which transforms to high impedance (greater than or equal to 500 ohms at 63.9 MHz) at the cable coil junction, preventing unbalanced shield currents from setting up a resonance in the coil. In one embodiment, a balun circuit may be provided by mounting a silver-plated copper braiding, 1.59 mm in OD, 19 AWG (Alpha Wire Company, USA) with heatshrink tubing onto the coaxial cable. The braiding may be contacted to the shield of the coaxial cable at the miniature RF plug (MMCX-50-12/111, Huber & Sulmer, Herisau, Switzerland). The electrical length of the braiding may be chosen to form a quarter wavelength, which transforms the short at the RF plug to high impedance at the cable coil conjunction. Shield currents are prevented from setting up a resonance on the coil, thus reducing heating effects. The braiding may be constructed to extend over the coil electronics and shield them. In this embodiment, advantageously the noise performance of the coil is improved, and signal inhomogeneities generated by the whole assembly acting as a rod antenna can be reduced. The length of the balun circuit in this configuration was determined to l=910 mm, and the resulting impedance was determined to Z=750 Ohms. The values specified herein are understood to be illustrative, with reference to the disclosed embodiment. It is understood that other values may be employed or achieved in other embodiments.

FIG. 7 depicts an embodiment of an imaging coil 104 adapted for use with the imaging system of the present invention. As shown in this figure, an inductor loop antenna 180 is formed on a flexible circuit 194 using a conductor such as a copper trace 188. In one embodiment, the inductor loop antenna 180 may be formed from a copper trace traced over a polyimide flexible circuit substrate. The copper trace may be coated with a polyimide layer to prevent oxidation during sterilization process and to maintain the integrity of the copper trace during used. As shown in this figure, pads 192 may be provided for the affixation of the capacitors and PIN diode previously discussed.

Figure 8:
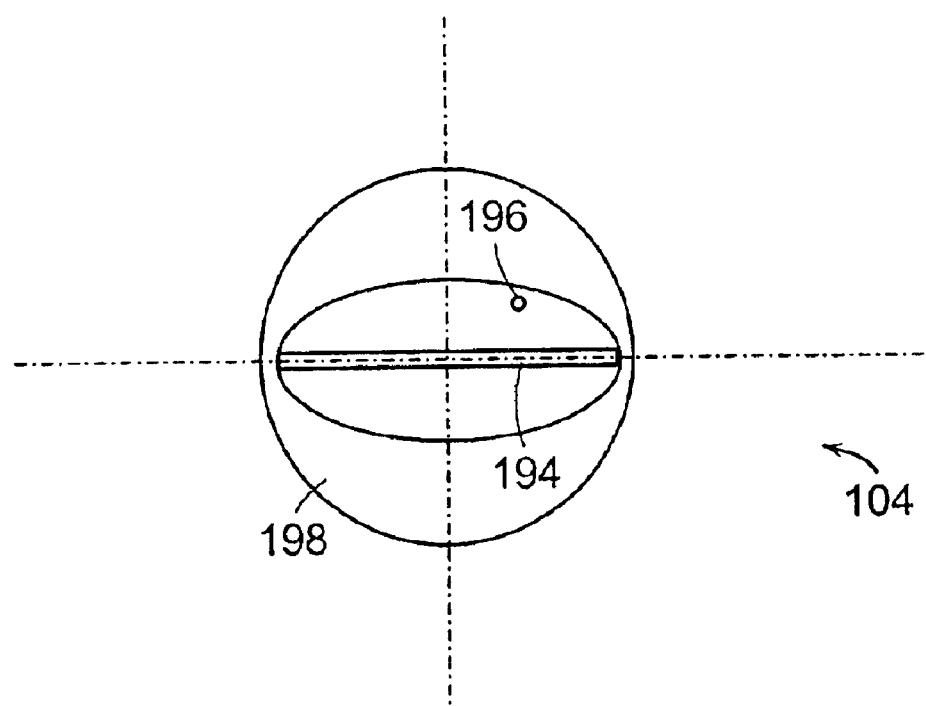
FIG. 8 provides a cross-sectional view of the lumen with an imaging coil therein.
Figures 9A, 9B:
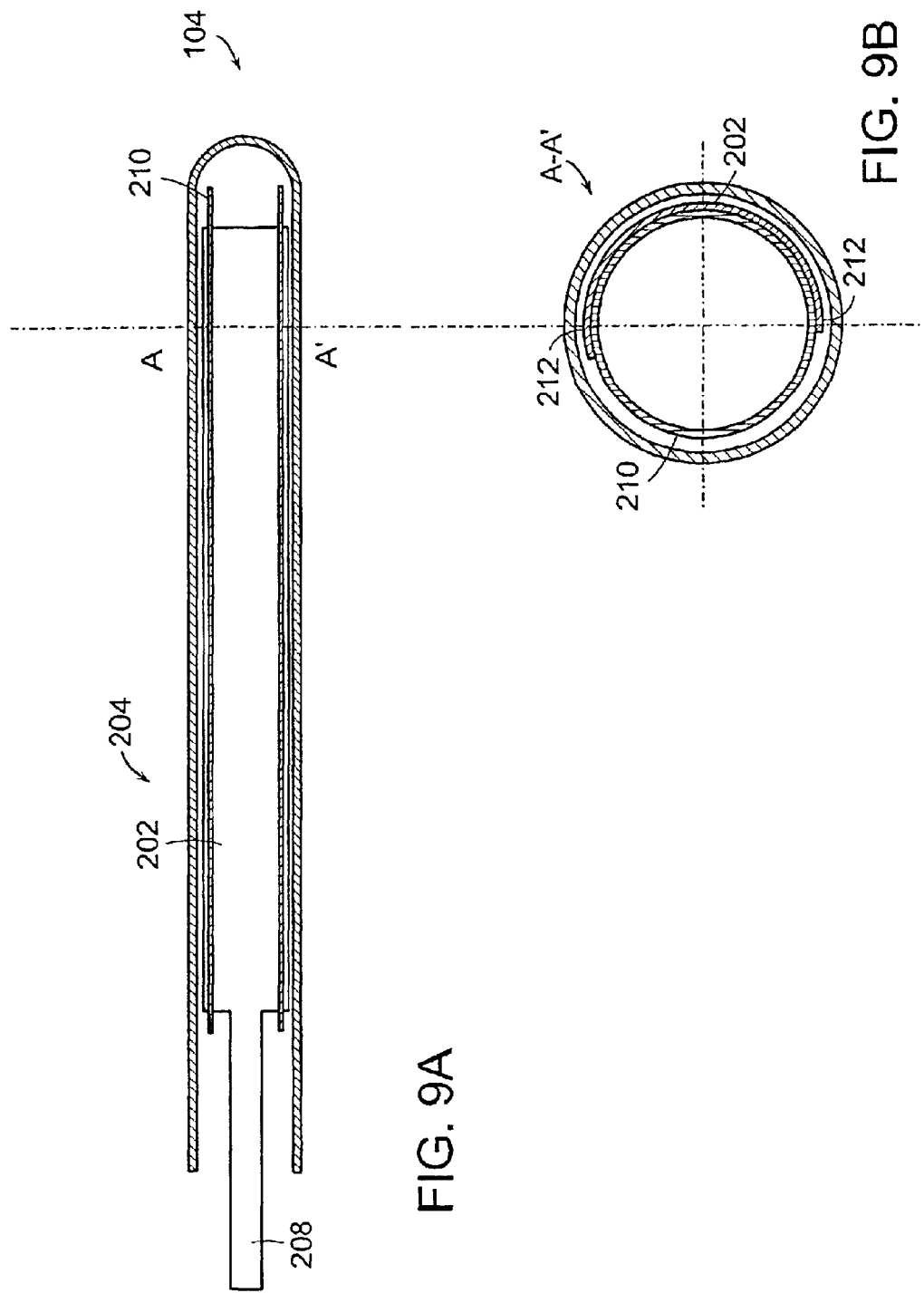
FIGS. 9A and B provide longitudinal and transverse cross-sections of an embodiment of an imaging coil system.
Figure 13:
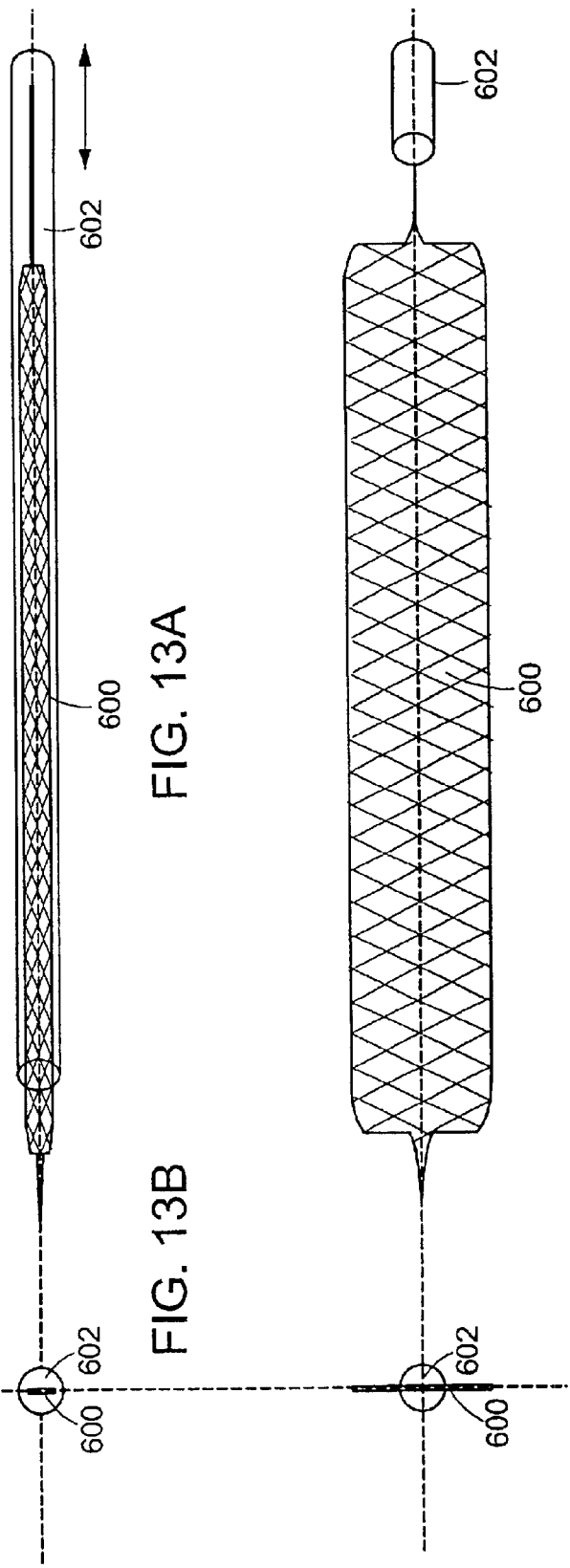
FIG. 13A-D provide longitudinal and cross-sectional views of folded and expanded decoupling paddles.

FIG. 8 shows one embodiment of an imaging coil 104 according to the present invention wherein the flexible circuit 194 upon which the imaging loop is formed may be contained within a polymeric housing 198 with an oval lumen 196. With this arrangement, the flexible circuit 194 lies flat in the oval lumen 196 with the parallel inductors (not shown) lying along the higher diameter of the lumen 196. Alternatively, as shown in FIGS. 9A and B, a flexible circuit may be shaped cylindrically or in any other shape consistent with the anatomy of the urethra. FIG. 9A shows a longitudinal cross-section and FIG. 9B shows a transverse section of an imaging coil 104. In FIG. 9A, an imaging loop flexible circuit 202 is shown to be housed within a polymeric tubing sealed at its distal end 204. Proximal to the flexible circuit 202 supporting the imaging loop is a section of the flexible circuit supporting the tuning-matching circuit and a decoupling circuit (not shown). The flexible circuit 202 is curled around an internal tubing 210. FIG. 9B shows this arrangement in more detail. The flexible circuit 202 is shown within the outer polymeric housing 204, curled around the internal tubing 210 to form a half-circle. According to the depicted embodiment, the copper traces 212 that are deployed upon the flexible circuit 202 as previously described are arranged approximately 180 degrees apart from each other. Holes (not shown) or other modifications of the flexible circuit 202 may be provided to facilitate its shaping. Other arrangements of a single imaging coil may readily be envisioned by practitioners of ordinary skill in the arts.

FIGS. 10A and B depict, respectively, a single imaging loop coil system and a double imaging loop coil system. As previously described, in one embodiment illustrated in FIG. 10A a single imaging loop coil system may include an imaging coil 104, a cable assembly 113 and an interface circuit that includes a tuning matching circuit 181 comprising a set of capacitors in series 182 and a set of capacitors in parallel 184, a decoupling circuit comprising a PIN diode 190, and a balun 112 included as part of the cable assembly. FIG. 10B shows a double imaging loop coil system where two separate imaging coils are positioned relative to each other. Distally, a single loop coil 104 from each imaging coil system is positioned orthogonally to the other. Proximally, the interface circuit for each imaging coil system comprises a tuning matching circuit 181 and a PIN diode 190, and the output from each interface circuit extends proximally through a coaxial cable 114 provided for each imaging coil system. A triaxial braiding layer that functions as a balun 112 surrounds the circuitry for the two imaging coil systems.

FIG. 10B depicts in more detail an electrical schematic of an entire quadrature coil assembly. The quadrature coil assembly is based on the single-loop design described above. This figure depicts two flexible coil circuits with placed orthogonal to each other in the polyamide tubing. Each coil may be separately tuned, matched, decoupled and connected to a separate coaxial line. The values of the serial 182 & parallel 184 capacitors, as well as the length of the coaxial line between the parallel capacitors 184 and the PIN diode may be kept the same as for the single-loop coil. In the depicted embodiment, the two separate coaxial lines may be joined inside a common λ/4 braiding which may be mounted with heatshrink tubing onto the cables. At the proximal end (i.e. the preamplifier end) of the coil assembly, the braiding may be connected to the outer conductors of the coaxial lines at the RF plugs and, therefore, to common ground. The distal end of the braiding may extend over the coils tuning and matching capacitors. In an illustrative embodiment, the length of the balun circuit in this configuration was determined to be l=930 mm, with the resulting impedance determined to be Z=770 Ohms.

As depicted in FIGS. 11A and B, minimization of the mutual inductance between the two coils may be in achieved by inserting a metallic decoupling paddle 500 between the imaging coils 502 and 504 arranged as a quadrature. FIG. 11A shows a longitudinal view of a quadrature imaging coil 510 embodiment according to the present invention, with the decoupling paddle 500 inserted between the two imaging coils 502 and 504. In the depicted embodiment, the decoupling paddle 500 consists of nonmagnetic braiding with a rectangular cross section (3×1 mm). However, the shape does not have to be rectangular as shown and the cross sectional area does not have to be rectangular as shown. As shown here, the paddle 500 may extend over the full length of the coils 502 and 504 (50 mm). Twisting the paddle along its longitudinal axis coaxial between the two coils steers the magnetic flux lines and can therefore influence the coupling between the coils in a very efficient manner. FIG. 11B shows the decoupling paddle 500 arranged at a 45° position relative to the coils 502 and 504, an arrangement that is particularly advantageous for effectively isolating both coils. Because coil 502 and coil 504 are placed orthogonal to each other, they may be already decoupled geometrically from another. Residual mutual inductance between the two coils, however, can lead to degradation of the signal homogeneity and decreasing signal penetration depth. The metallic, non-magnetic decoupling paddle 500, when inserted into the region between the two coils 502 and 504, steers the magnetic flux. Twisting the paddle 500 along its longitudinal axis into a position close to the 45° position as shown, may effectively decouple the mutual inductance between the coils 502 and 504. With this means, the coils 502 and 504 can be isolated more than 50 dB. Alternatively, the two coils of the quadrature design can be combined using a quadrature hybrid coupler for use as a quadrature surface coil, or the two coils can be used separately with a multicoil system as phased-array coils, without the quadrature hybrid coupler. A dual phased array connection method may maintain the √2 increase in SNR that may be theoretically obtained with a quadrature configuration, and also may allow imaging at any oblique orientation without a loss in the signal intensity.

As shown in more detail in FIG. 12, single-loop coils 502 and 504 may be placed orthogonal to each other. Coil 502 is tuned to the magnetic resonance frequency of protons and matched to the input impedance of the receiver with the aid of the capacitors 512 and 513, respectively. The endoluminal receive coil is decoupled from the radiofrequency (RF) transmitting body coil during RF transmission with an actively switched PIN diode 518. Coaxial line 522 connects receive coil 501 to the surface coil port of the scanner. Coil 504 is individually tuned and matched and decoupled with 514, 515 and 520 respectively. Coaxial line 524 connects receive coil 504 to the surface coil port of the scanner. Both coils can either be connected as phased array or, alternatively, as quadrature receive coils. The assembly can be connected as transmit or transmit/receive coil by omitting the PIN diodes 518 and 520.

In certain embodiments, as depicted in FIGS. 13A–D, the decoupling paddle 600 may be designed to be self-expandable. It can thus be applied even in very small diameter coil applications, i.e. endovascular, endourethral, transoesophagal, rectal, etc. In the folded state, shown in FIG. 13A (side view) and FIG. 13B (front view), the coil(s) (not shown) and the paddle 600 are contained in an introducer sheath 602. In this state they can be introduced into the body and, placed at the tissue under investigation, they can be deployed by retracting the catheter sheath 602, shown schematically in FIGS. 13C and 13D. The self-expandable coils and paddle 600 may then unfold at the target tissue for imaging. The frame of the paddle 600 and the loop coil can be manufactured from any electrical conducting, flexible metal alloy, such as Nitinol for example. To be self expandable, the paddle 600 may be constructed from any metallic braiding.

Figure 14:
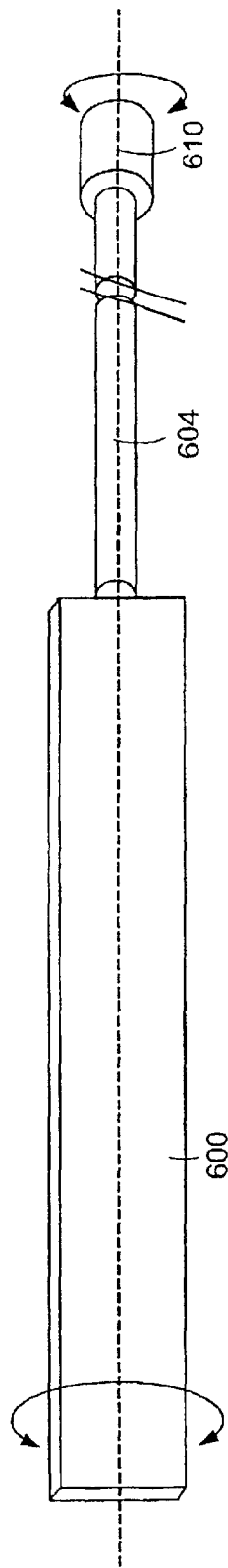
FIG. 14 provides a schematic diagram of a remotely manipulable decoupling paddle.

As shown in FIG. 14, the decoupling paddle 600 can be designed such that remote decoupling and fine-adjustment is possible. When attatched to a (flexible) activation rod 604, the paddle 600 and the coil (not shown) may be carried in a catheter or introducer (not shown) with the activation rod 604 running, for example, through the working channel of the catheter or introducer 602. The rod 604 may then be manipulated by controls placed on the proximal end of the catheter system, for example, by twisting a handpiece 610 at the proximal end of the rod to deliver a torque to the paddle 600 affixed to it distally, thereby permitting fine adjustments of paddle position and coil isolation.

The maximum paddle size is restricted by the space between the coils to be decoupled. The paddle can be used for any combination of two or more receiver or transmit coils, especially for an endocavitary use including endourethral, endorectal, transoesophagal, endovascular, endovaginal, and other endocavitary anatomic sites. Paddles can be used in conjunction with any coil design known in the art, i.e. quadrature, phased array, birdcage, etc. A decoupling paddle may be adapted for use with very small and slim coil designs such as intravascular or endourethral positioning. A decoupling paddle, as described above, can be flexible or self-expandable using shape memory metallics such as Nitinol. In other embodiments, the decoupling paddle can be manipulated remotely through catheters or introducers using remote tuning mechanisms such as a flexible rod. Decoupling paddles may be made from a variety of materials. In certain embodiments, metallic braid, preferably non-magnetic, may be used to form the paddle. In other embodiments, paddles may be made from hollow tubing and shaped as ovals, as rectangles or as other shapes longitudinally orientable between the coil assemblies. Other arrangements of decoupling paddles and similar decoupling structures may readily be envisioned by practitioners of ordinary skill in the art.

3. System Adapted for Visualization of the Male Urethra and Prostate

Modifications of the embodiments described above permit the adaptation of these systems and methods to the evaluation of the male urinary tract including the prostate. In one embodiment, an imaging coil according to the present invention may be inserted in the male urethra and positioned near the prostate. As previously described, signals picked up by the coil may be conducted through an interface circuit that includes a tuning-matching circuit, a decoupling circuit, and a balun circuit, to be connected with the surface coil port of an MRI scanner or such as the GE 1.5T scanner, or any other MRI system. In one embodiment, the system adapted for the male urethra may be housed in a polymeric tubing similar to a standard Foley catheter to prevent direct contact with the tissue.

The imaging coil system for use in the male urethra according to the present invention may include an imaging loop coil, and interface circuit comprising tuning-matching, decoupling and balun circuits, a housing enveloping the imaging loop coil, and an external shielded box housing the balun and DC regulating circuit. In one embodiment the imaging coil may include a copper trace etched on a flexible circuit. The copper trace may be coated with a polyimide layer or any other layer that serves to prevent oxidation during the sterilization process and to maintain the integrity of the copper trace during use. The tuning-matching capacitors and may be mounted on the proximal and distal end of the flexible circuit to adjust the output of the coil to 50 ohm impedance. In one embodiment, the decoupling circuit may be built on the flexible circuit so as to be tuned the coil during RF transmission by the body coil and thereby avoid decoupling artifacts (imaging artifacts), and further prevent heating during clinical use. In one embodiment, it is anticipated that the distal 5–20 cm of the coil will be inserted into the urethra and directed through the urethra proximally toward the prostate. The remaining length of the coil and interface box will remain outside the body.

Figure 15A:
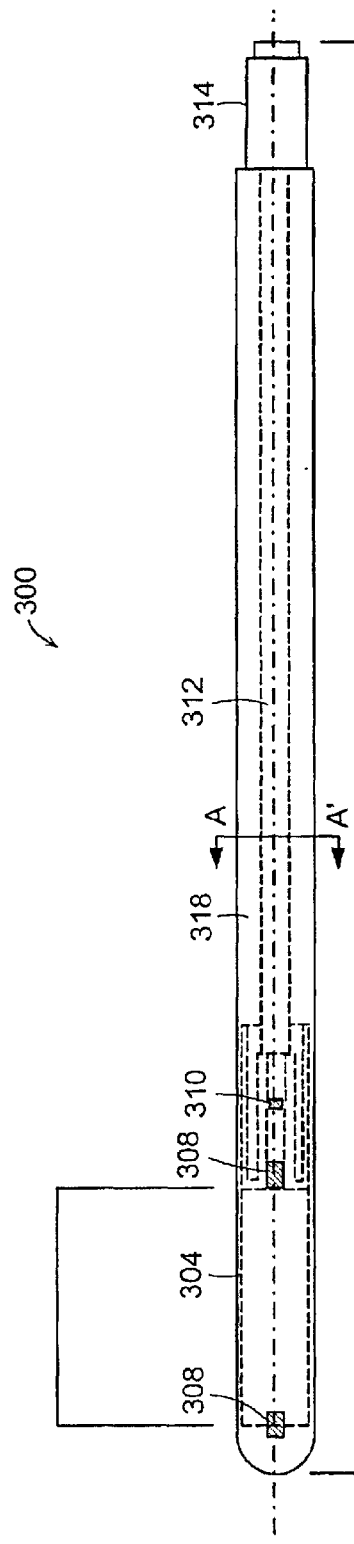
FIGS. 15A and B provide a schematic diagram of an embodiment of an imaging coil adapted for use in a male urethra.
Figure 15B:
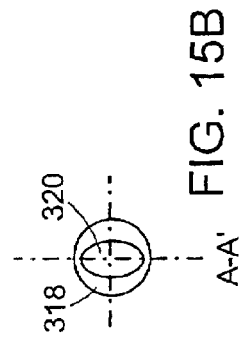

FIGS. 15A and B depicts an embodiment of an imaging coil 300 according to the present invention advantageous for evaluating the male urethra, the prostate, and the surrounding tissues. In this Figures, a flexible circuit antenna 304 is shown housed in a polymeric housing 318. In one embodiment, the housing 318 is provided with an oval lumen 320, shown in the cross-sectional view of FIG. 15B taken at the line a–a' on FIG. 15A. The orientation of the oval lumen 320 maintains the flexible circuit antenna 304 in a preselected orientation with respect to the patient's urethra and periurethral tissues. As has been previously described, the flexible circuit antenna 304 may include a copper trace etched on a flexible circuit that acts as the MR imaging coil. In one embodiment, the flexible circuit may be a single flexible circuit about 11 cm long. Also shown in FIG. 15A are other components of an MR imaging system according to the present invention. In this embodiment, tuning-matching capacitors 308 may be soldered onto the proximal and distal end of the imaging coil circuit to adjust the output of the coil to 50 ohm impedance. The output impedance of the coil 300 is matched to 50 ohms at 63.9 MHz, understood to be the frequency of the signal generated by the hydrogen protons. Impedance matching at 63.9 MHz, performed in a physiological saline solution, is accomplished by using two sets of capacitors, one in series (capacitance=75 pF) in the other in parallel (capacitance=351 pF). One or more capacitors can be used to achieve their acquired capacitance. The pads for the capacitors maybe etched on the proximal and distal part of the imaging loop flexible circuit 304. In one embodiment, "A" tape ceramic, non-magnetic, surface mount capacitors maybe used to match the output impedance to 50 ohms in a physiological saline solution at 63.9 MHz. The output from the tuning-matching circuit may be transmitted to the preamplifier (not shown) through a decoupling and a balun circuit. An active decoupling circuit for the depicted embodiment comprising a diode 310 may be built into the same flexible circuit to detune the coil during RF transmission by the MRI body coil, thereby to avoid decoupling artifacts in the images acquired and to prevent temperature increase in the area where the coil is positioned during clinical use. In one embodiment, the distal 5–20 cm of the imaging coil 300 may be inserted into the urethra. The remaining length of the coil 300 will remain external to the body. Located at the proximal end of the imaging coil 300 in the depicted embodiment may be a connector 314 such as a micro-BCN connector. This connector 314 permit attachment of the imaging coil 300 to an interface box (not shown). The imaging coil 300 may be connected to the interface box (not shown) by a micro coaxial cable 40 cm long. The micro coaxial cable may be terminated in a micro coaxial connector which is connected to the receptacle on the interface box. The decoupling circuit section of the flexible circuit 304 may be insulated by drawing a polyester heat shrink tubing over it. A tin-plated copper braiding, which is electrically connected to the shield of the micro coaxial cable, may be provided to shield the decoupling circuit during RF transmission of the MRI body coil. In addition to the polyester insulation, a thin layer of UV cure adhesive may be applied over the solder joints for mechanical stability and electrical insulation.

Figure 16:
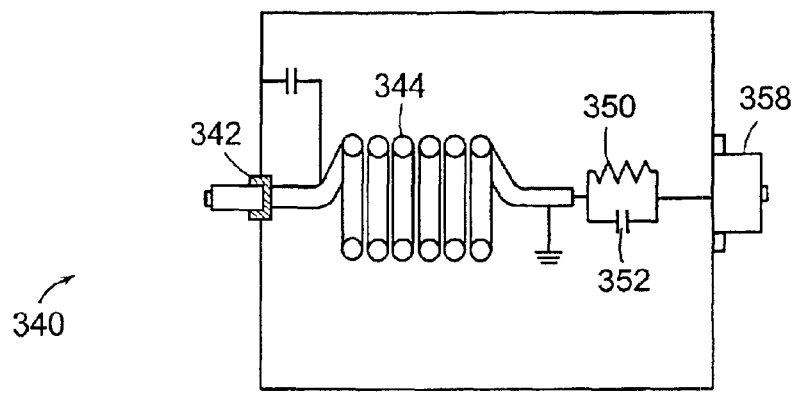
FIG. 16 provides an electrical schematic of an interface box.

FIG. 16 provides a schematic of an interface box 340 adapted for use with the previously described imaging coil 300. At the distal end of the interface box 340, a micro BNC connector 342 may be used to attach to the imaging coil described above. The interface box is a RF shield box housing the balun and the DC regulating circuit. The balun circuit comprises a coaxial cable inductor and a capacitor connecting the ground to the case. The electrical properties are adjusted so that a high impedance is provided at the cable coil junction, preventing unbalanced shield currents from setting up a resonance in the coil. Signal is conveyed into the interface box 340 where it passes through a cable trap 344 and thence to a DC regulating circuit comprising a 332 ohm resistor 350 and a 1000 pF capacitor 352 in series with the coil. The resistor 350 and a capacitor 352 are parallel to each other. The capacitor 352 acts as a DC block, diverging the magnitude of DC current to the diode, however, the capacitor 352 acts as a short to RF signal, not affecting the SNR performance of the coil. At the proximal end of the interface box 340 is a connector 358 such as a BNC connector, adapted for attaching the imaging coil to the MRI machine. While at present it appears advantageous to provide a separate interface box at the proximal end of the imaging loop system for the male urethra, other arrangements to provide interface circuitry and connectability may be substituted for the exemplary features described above without departing from the spirit and scope of the present invention.

4. Systems Combining Diagnostic and Therapeutic Applications

The systems and methods of the present invention may be used in combination with therapeutic modalities for urethral prostate and other pelvic conditions. A variety of embodiments combining a urethral coil for imaging and guiding therapy with therapeutic modalities may be envisioned by practitioners of ordinary skill in the art. In certain embodiments, the imaging coil may be built into an endourethral catheter similar to a Foley catheter. It will be understood by skilled practitioners that the imaging coil can be built into the Foley catheter in various ways, for example in the form of different configurations of imaging sleeves as described in the U.S. patent application entitled "Apparatus, Systems and Methods for In Vivo MRI," filed on Mar. 26, 2001, the contents of which are incorporated herein by reference. Other modifications of a Foley catheter may be used to transport the imaging coil system of the present invention into proximity with tissues to be examined.

Figure 17A:
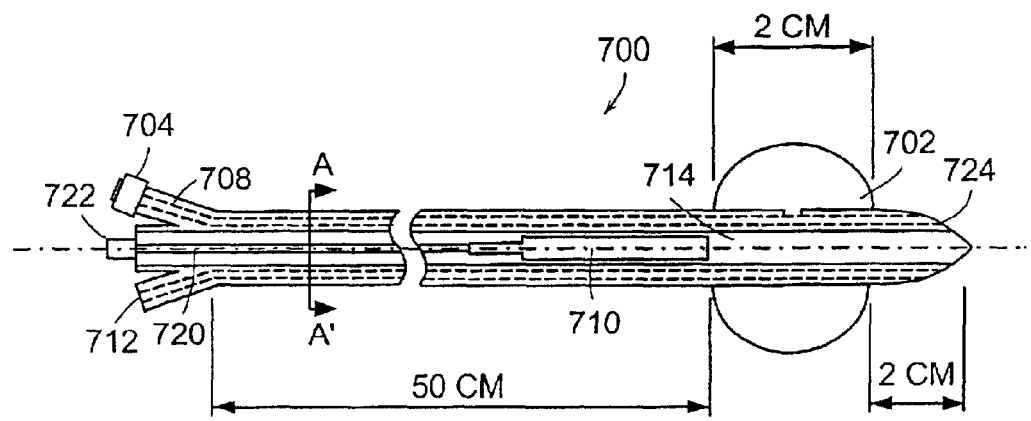
FIGS. 17A and B depict an embodiment of an endourethral imaging system.
Figure 17B:
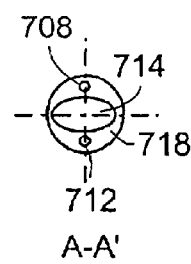

FIG. 17A depicts one embodiment of an endourethral catheter 700 bearing imaging coil 710 according to the present invention. A standard Foley catheter may be modified to house the imaging coil 710. In the depicted embodiment, a modified Foley catheter may be seen with standard Foley catheter features such as an inflatable balloon 702, and inflation port 704, and inflation channel 708, and a drainage lumen 712 used for draining urine or other body fluids. In the depicted embodiment, there is a central lumen 714 coaxially deployed along the length of the endourethral catheter 700. In this lumen is located an imaging coil 710, connected to a coaxial cable 720 as has been previously described. In the depicted embodiment, the coaxial cable 720 connects to a coaxial connector 722 that permits interface with the rest of the MRI system (not shown). In the depicted embodiment, the inflation channel 708, the drainage lumen 712 and the central lumen 714 are contained within the polymeric wall 718 of the endourethral catheter tubing. The tip 724 may be configured to facilitate passage of the endourethral catheter 700 into and through the urethra. FIG. 17B shows a cross-section of the endourethral catheter 700 taken at the level A–A' on FIG. 17A. In this cross-section, the central lumen 714 is noted to be of oval shape. In an illustrative practice of the methods of the present invention, the imaging loop 710 may be placed in the endourethral catheter 700 within a central lumen 714 proximal to the balloon 702. The catheter 700 made then be advanced through the ureter into the bladder. The balloon 702 may be inflated to lock the catheter 700 in place. Fluids may drain through the drainage lumen 712, or this lumen 712 may serve as an access route for injecting drugs or contrast agents into the bladder. An endourethral catheter 700 according to the present invention may be designed and modified to enable the performance of transurethral image guided therapeutic procedures under MRI. Transurethral procedures that may be carried out for prostate treatment include, for example, microwave treatment for prostatic hypertrophy, injections with dehydrated ethanol, laser ablation of the prostate, transurethral incision of the prostate, transurethral needle ablation, and transurethral stent placement. Procedures that may be carried out for treatment of urinary incontinence include, for example, transurethral placement of collagen, silicone, calcium hydroxyapatite particle injections, etc. Other procedures may be envisioned by skilled artisans to treat urethral, periurethral and pelvic disorders using these systems and methods.

As will be understood by skilled artisans, an intraurethral therapeutic device according to the present invention may comprise an elongate member insertable into a urethra of the patient and temporarily retainable therein which houses an endourethral imaging system and an endourethral therapeutic system. As previously described, the endourethral imaging system may comprises an endourethral MRI coil comprising an antenna, and an endourethral delivery device to deliver a mode of therapy transurethrally to an area of the anatomic region imaged by the endourethral imaging system. The elongate member may be temporarily retained in a preselected position by an inflation of a balloon or by any other retention mechanism familiar to ordinary practitioners in these arts. In certain embodiments, the mode of therapy delivered comprises electromagnetic radiation. The electromagnetic radiation may comprise light energy, heat energy or any other form of electromagnetic radiation. The electromagnetic radiation may comprise laser-generated light, microwave energy, infrared radiation or ultraviolet radiation. Other modes of therapy are also contemplated that include pharmacologic agents. A variety of pharmacologic agents will be familiar to skilled artisans, including anti-neoplastic agents, anti-inflammatory agents, antibiotics, hormones, radiation sensitizers, and a variety of other agents active against the conditions found in the tissues surrounding the subject urethra. In one embodiment, the pharmacologic agent comprises a radiation source. Certain radiation sources are already familiar in the art, including radiation seeds and other radiation implants. Radiation sources and other pharmacological may also be added to implantable devices to be implanted according to the systems and methods of the present invention. In one embodiment, the mode of therapy comprises an implantable device. A variety of implantable devices may be envisioned by skilled practitioners as falling within the scope of the present invention, including as examples, stents, conduits, valves, implants, drains, tubes, films and implantable or sustained-release drug delivery systems.

An endourethral catheter system according to the present invention may be adapted to the diagnosis of urinary incontinence and related disorders. For example, pressure and fluid sensors may be positioned and different sections of the catheter, and contrast agents may be injected into the bladder through the drainage lumen. These techniques may combine the diagnostic methods of the imaging coil 710 with more traditional urodynamic studies to provide additional information for accurate diagnosis of urinary incontinence. According to one diagnostic method, fluid pressure in the bladder may be measured along with pressure at different points in the urethra to assist in understanding the changes in fluid pressure at the different sites; these measurements may be correlated with simultaneous real-time imaging using imaging coil 710 which could observe the bladder and pelvic floor changes during the procedure.

Figure 18:
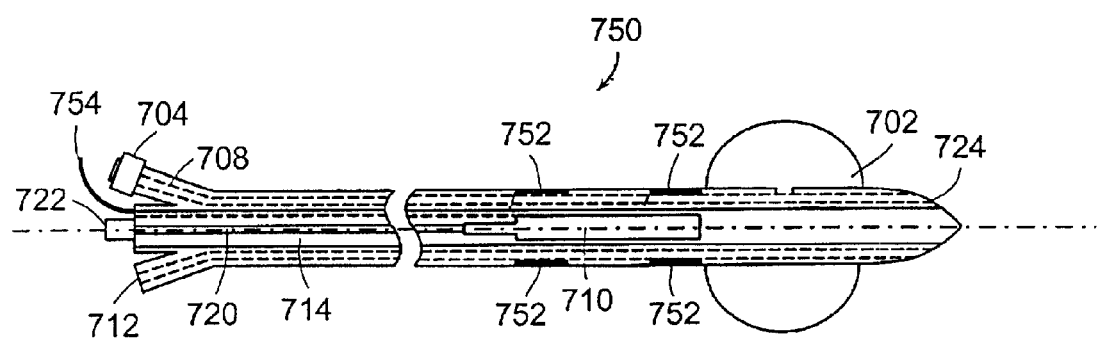
FIG. 18 depicts an endourethral imaging system combined with RF ablation.

FIG. 18 depicts an endourethral catheter systems 750 adapted for microwave ablation of the prostate and similar procedures. In the depicted embodiment, an imaging coil 710 is positioned within the central lumen 714 of an endourethral catheter 750. As in previous figure, a drainage lumen 712 is available, as well as an inflation channel 708 and inflation port 704 for inflating a balloon 702. Similar to the previous figure, the imaging coil 710 is attached at its proximal end to a coaxial cable 720 that then attaches to a coaxial connector. The depicted endourethral catheter system 750 includes at least one RF/microwave ablation coil 752 on the surface of the catheter system. The RF ablation coil may have two coils, positive and ground. In one embodiment, these coils 752 may be placed between 2–6 centimeters apart, depending on the size of the prostate area being treated. In one embodiment, the length of the ground and positive coils may be from about 0.1 cm–2 cm. In other embodiments, the positive coil may be on the endourethral catheter system 750 with the patient is the ground. Similar to the depicted embodiment, an endourethral catheter system may substitute ultrasound treatment for the microwave ablation described above. In such an embodiment, the microwave coils 752 would be replaced by a set of ultrasonic transducers with one or more transducers being placeable on the coil. These embodiments may improve the clinical outcome for treatment of benign prostatic hypertrophy, where the ablation method can open up the urethra that is blocked by the hypertrophic prostate. Transurethral resection of the prostate may be carried out under cystoscopic or transrectal ultrasound guidance. The outcome for both these procedures may be significantly improved if high-resolution MR imaging is used for guiding them.

Figure 19:
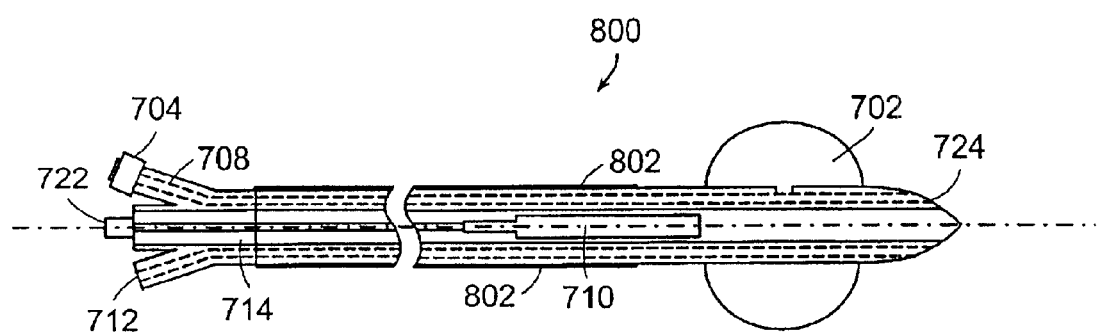
FIG. 19 depicts an endourethral imaging system combined with laser ablation.

FIG. 19 depicts an endourethral catheter system 800 adapted for endourethral image guided laser ablation of the prostate. In the depicted embodiment, the endourethral catheter system 800 includes previously described features such as a drainage lumen 712, a balloon 702 with an inflation port 704 and inflation channel 708, an imaging coil 710 attached proximally to a coaxial cable 720, and a coaxial connector 722 attached to the coaxial cable 720. External to the polymeric tubing 718 of the endourethral catheter 800, a sheath 802 is provided that carries laser energy to be directed toward specific regions of the prostate as necessary. The sheath 802 may be a laser delivery guide that is divided into multiple sections so that laser energy delivery to each section may be externally controlled. Image guidance received through the imaging coil 710 may be analyzed by the physician to determine to which sections of the laser bearing sheath 802 the laser energy may be turned on or off. In a procedure involving the systems and methods of the present invention, the endourethral catheter system may be inserted through the urethra and retained in the bladder by inflating the balloon 702. The imaging coil 710 would then permit the imaging of the urethra and prostate. According to those images, the position of the endourethral catheter 800 may be adjusted so that the sheath 802 would be appropriately positioned to ablate the regions of interest. Laser energy may then be guided to the sections of the prostate or other tissues to be ablated. In other embodiments, fiber-optic bundles may be incorporated in the polymeric wall 718 or may be carried in other ways on the wall of the endourethral catheter 800 so that laser energy could be delivered to the prostate or other tissues of interest. While the depicted embodiment features an endourethral catheter system 800, the present invention may employ any suitable elongate member for traversing the urethra and for positioning the endourethral diagnostic and therapeutic systems. As will be understood by practitioners in the art, the elongate member of the present invention may comprise a multiple lumen catheter or a set of catheter systems, either single-lumen or multilumen. The elongate member further can comprise a partially or completely solid article within which the endourethral diagnostic and therapeutic systems are contained. Other arrangements of the diagnostic and therapeutic members with respect to the elongate member of the present invention will be apparent to practitioners of ordinary skill using no more than routine experimentation.

In certain embodiments, the endourethral therapeutic system of the present invention may be affixed to or carried on an outside surface of the elongate member. In certain embodiments, the endourethral therapeutic system is temporarily affixed to the outside surface and is displaceable therefrom. The endourethral therapeutic system may be contained within a surrounding layer applied external to the elongate member in certain embodiments. In other embodiments, the endourethral therapeutic system may be contained within said elongate member. In a particular embodiment, the elongate member may comprise a hollow tubular member. The endourethral therapeutic system may be contained within said hollow tubular member. In one embodiment, the endourethral therapeutic system may be displaceable from a first position within said hollow tubular member to a second position external to said hollow tubular member. In another embodiment, the delivery device may become activated for delivering the mode of therapy when the endourethral therapeutic system is displaced from the aforesaid first to the aforesaid second position.

The systems and methods described herein are for illustrative purposes only. Other combinations were the diagnostic techniques of the present invention may be joined with therapeutic modalities, especially those using electromagnetic energy, may readily be envisioned by practitioners of ordinary skill in the art.

EXAMPLES

Example 1

Heating Properties

Heating experiments were performed with the coil inserted into agar gel (DIFCO Laboratories, Franklin Lakes, N.J.) phantom doped with 0.45% NaCl to mimic the electrical properties of the body. The conductivity of the gel was measured to be 0.8 S/m at 64 MHz, a median value in the range of human tissues. Temperature was monitored with an eight-channel flouroptic thermometer (UMI 8, FISO Technologies, Inc., Quebec, Canada). Five sensors were equally spaced and placed adherent to the outer coil tubing along one conductor of the single-loop coil. Thus, two sensors had direct contact with the distal and proximal edge of the flexible circuit. A sixth sensor was placed at the opening of the balun circuit.

The specific absorption rate (SAR) was calculated by finding the initial slope of the temperature rise (dT/dt) and multiplying by the specific heat capacity of the agar gel, C=4180 J/kg. Scanning was performed on a 1.5 T Signa LX(GE Medical Systems, Milwaukee, Wis.), transmitting with the body coil. The scanning parameters were: fast spoiled gradient echo sequence (FSPGR: axial sections, flip angle 122*, TR/TE 5.8/1.9 ms, FOV 480×480 min, matrix 256×128, 113 NEX, BW 31.25 kHz, 4 slices each 10 min, 10 min spacing, imaging time 9:56 min). The transmit gain was intentionally increased by 7.2 dB above the value selected by the scanner calibration software to obtain the maximum transmit gain available from the scanner. The scanning parameters resulted in a peak SAR of 3.96 W/kg and a mean SAR 1.98 W/kg. The phantom and cables were kept parallel to the main axis of the scanner bore. The cables were elevated to the isocenter of the magnet and moved laterally until they were as close to the bore wall was possible (8 cm), as constrained by the size of the phantom. This position gives near maximal heating (25). For each tested position the coil was disconnected to simulate a worst case with disabled detuning of the intraluminal coil.

None of the tested cases resulted in excessive heating beyond the local SAR limits (Table 1) based on the current International Electrochemical Commission (IEC) 60601-233 standard: 8 W/kg in any gram of tissue in the head or torso for 15 minutes.

Example 2

In Vitro Testing

Imaging was performed using the body coil of the scanner as RF transmitter and the endourethral coils as receive-only probes. For assessing the signal characteristics of the antennas, protondensity (PD)-weighted axial and coronal images were acquired with a fast spin-echo (FSE) sequence (PD-FSE: 8 echoes, TR/TE=2000/14.5 ms, BW=15.6 kHz, 6 NEX). Axial 3 min sections with a 30×30 min field of view (FOV) and a 256×128 matrix as well as coronal 2 min sections with a 80×80 min FOV and a 256×128 matrix were collected in 3:24 min.

The coils' imaging performance was evaluated in one formalin fixated as well as in six freshly harvested female human cadaver pelvices. The coils were subsequently introduced into the urethra with the tip entering the bladder by approximately 5 mm. This position ensured the whole urethra and the internal sphincter to be covered by highest signal intensity and homogeneity of the coil. For localization purposes, a 5"×9" rectangular shaped surface coil was employed from outside the body to give gross orientation of the small pelvis anatomy. This coil was disabled for subsequent high-resolution imaging with the endourethral coils. Following double oblique sagittal and coronal fast spoiled gradient FSPGR localizer imaging with large FOV's, high-resolution PD and T2-weighted imaging of the whole urethra was acquired in a plane axial oblique to the urethra coil. The spatial in-plane resolution was progressively increased by consecutive reduction of the FOVs from 40×40 mm to 30×30 mm and finally to 20×20 mm.

The signal intensity of images acquired with small endoluminal imaging probes is highly non-uniform due to the B, inhomogeneity of the pick-up device. High sensitivity of the receiver coil in its immediate vicinity and especially close to the coil conductors leads to a signal saturation in these areas, whereas the signal drops off with roughly $1/r^2$ with increasing radius, r, away from the coil. It is difficult, if not impossible, to see all the parts of the images at any one time by adjusting the contrast and brightness of the images. A solution to this problem is to calculate a uniform signal intensity image by dividing the image intensity by the corresponding sensitivity map of the coil. In this case, noise on the images is not uniform and will increase toward the periphery of the image, but a single brightness and contrast level can be used for a convenient display of the central parts of the image (20). The applied display method reads an image, derives the main magnetic field orientation with respect to the imaging plane, and assumes that the coil is perpendicular to that plane. Coil positions and angles can be entered interactively.

Results of Examples 1 and 2

For each position of the coil/phantom in the scanner, the temperature increases from sensor 1 to sensor 5, i.e. from the inside of the phantom to the edge of the phantom (Table 1).

TABLE 1

SAR rise within 10:00 min of scanning at five different locations along the coil. The imaging region of the coil as well as the mouth of the coaxial choke were inserted into agar-gel by approximately 75 mm. Positions of the coil/phantom in the scanner were: a) middle of bore, coil connected, b) middle of bore, coil disconnected, i.e. decoupling disabled, c) close to scanner bore, coil connected, and d) close to scanner bore, decoupling disabled.

| Position of coil | SAR [W/kg] Sensor 1 | SAR [W/kg] Sensor 2 | SAR [W/kg] Sensor 3 | SAR [W/kg] Sensor 4 | SAR [W/kg] Sensor 5 | SAR [W/kg] Sensor 6 |
|---|---|---|---|---|---|---|
| a) | 0.63 | 0.67 | 1.05 | 1.26 | 1.68 | 1.54 |
| b) | 1.12 | 1.12 | 1.75 | 1.68 | 1.82 | 1.70 |
| c) | 1.68 | 1.4 | 1.82 | 2.31 | 2.45 | 2.07 |
| d) | 3.78 | 3.78 | 4.34 | 5.04 | 5.32 | 4.32 |

The temperature increases when the coil is disconnected from the scanner surface coil port, i.e. when the decoupling of the receive coil is disabled (Table 1, pos. b). The temperature increases when the phantom/coil is moved towards the scanner bore, i.e. closer to the RF transmitting body coil (Table 1, pos. c). Positioning the phantom/coil close to the wall of the scanner bore and disconnecting the coil from the surface coil port (Table 1, pos d) gives maximal heating and SAR (1.33 C/5.32 W/kg) at the proximal edge (sensor 1) of the imaging coil.

Introduced into saline solution, the single-loop coil showed good axial signal homogeneity over the full circumference of the coil. The near-field of the coil reveals two high signal spots direct at the coil conductors. The quadrature receiver coil showed improved axial signal homogeneity and signal penetration depth when compared to the single-loop configuration. Removing the decoupling paddle from the quadrature coil configuration results in drastically decreased performance of the coil. Coupling between the coils leads to poor signal homogeneity and decreased penetration depth. The longitudinal signal distribution is homogeneous over almost the full length of the coil (data not shown).

Besides the reduction of heating effects, the implementation of a balun circuit into the overall design resulted in an improvement of the coil homogeneity and thus image quality. Two effects are believed to be accountable. First, the braiding of the balun circuit was extended over the coil tuning and matching capacitors, shielding the resonant components towards the outside and thus reducing the inherent noise of the receive coil configuration. Second, the balun circuit limited induced currents on the outer shield of the coaxial cable, acting as a rod antenna which couples to the electric field of the RF, comparable to the loopless catheter antenna. These induced currents potentially interact with the $B_1$ field of the coil, diminishing its homogeneity.

The use of a metallic "paddle" to steer the magnetic flux of a coil as a means to insulate two adjacent coils from each other was first published in the literature in 1946 and was then reconsidered by others. In these publications, however, a rather small paddle was used to decouple large volume coils from one another, trying to minimize distortions of the $B_1$ field homogeneity to the inside of the coil. The application of such a paddle to an 'inside out' design of endoluminal coils as described herein enabled the paddle to be inserted into the most sensitive region inside between the coils. Furthermore, the paddle could be designed larger in comparison to the size of the coil, providing a very effective means of coil insulation, without virtual affecting the $B_1$ field towards the outside of the coil. No additional electronics were required to achieve an isolation of about 50 dB. Image quality was markedly improved by minimizing the mutual inductance between the coils. Without the paddle inserted, the signal performance of the quadrature coil was inferior compared to that of the single-loop coil due to the interaction between the two coils.

Despite the inherent signal inhomogeneities of single-loop coils, showing two bright signal hot-spots in axial views which are generated by the two coil conductors, this design already showed a good axial signal homogeneity. The overall homogeneity and signal penetration depth of the single-loop was surpassed by the quadrature coil configuration, which produced an almost circular axial $B_1$ field.

Example 3

Cadaver Studies

The acquisition of axial and sagittal localizer images with the body coil and with the urethral coil inserted into the urethra reveals no increased signal adjacent to the intra urethral coil. This indicates that the decoupling circuit reliably detunes the receiver coil during body coil transmit. The sagittal slice shows the urethral coil in its final position for high resolution imaging, with the tip of the coil being inserted into the bladder by approximately 5 min.

High-resolution T2-weighted fast spin-echo images acquired in a sagittal plane enable the visualization of the urethra in its full length. The signal characteristics along the longitudinal axis of the coil ensured coverage of the full length of the urethra with high and homogeneous signal. Signal penetration depth is sufficient to show adjacent structures like the pubic bone and the wall to the rectum.

On PD and T2-weighted axial images, a multilayered appearance of the urethra was seen. Although the PD-weighted images revealed a markedly higher SNR, the soft tissues of the urethra were better demonstrated on the T2-weighted images. Therefore the focus of this study will be on the generated T2-weighted images.

Small FOV (30 mm) axial T2-weighted fast spin-echo images enabled the visualization of four layers of the urethra in high-resolution. The fluid filled urethral lumen had a bright signal. The mucosa of the urethra was also hyperintense on T2-weighted images and indistinguishable from the fluid. Surrounding the lumen, a circumferential hypointense layer was identified which is believed to correspond to the submucosa. A hyperintense thicker layer, corresponding to the smooth muscle, encircled the urethra. The hypointense layer, surrounding the smooth muscle layer, represented a dense connective-tissue layer. The achieved in-plane resolution was 94×156 μm while the slice thickness was 1.5 mm. For the given sequence parameters, the urethra was found to lie within the near-field of the coil, which provides high SNR. Signal penetration depth beyond the urethra was sufficient to depict the vagina posterior to the urethra. Post-processing and display of the images with an image intensity correction reliably removes signal inhomogeneities and hot spots due to the coil conductors, thus facilitating the visualization of structures adjacent to the coil. Image contrast increased by the removal of the coils B, signal profile, resulting in better depictability of the different urethra wall layers. Structures within the smooth muscle layer, previously hidden behind signal saturation on the T2 images can be resolved after application of the image intensity algorithm.

Further decrease of the FOV to 20 min while increasing the spatial resolution to 78×78~tm, enables the resolution even of single folds of the urethral mucosa. Once more, the image intensity correction was found to be helpful to enhance image contrast and to resolve coil adjacent structures.

The small diameter and the semi-flexible, cylindrical design of the coils enabled easy insertion into the cadavric female urethra. Additionally, the design allowed a stable positioning of the coil within the urethra, relative to the periurethral tissues. The length of the coils was sufficient to cover the full length of the urethra with high and homogeneous signal. The conductor separation of 4 mm provided sufficient signal penetration depth into the tissue to image the full axial extent of the urethra understood to be with high spatial resolution. Moreover, signal beyond the urethra enabled the examination of periurethral tissues. The introduction of a semi-flexible device with an OD of 15 F into the urethra itself, however, limits, if not precludes the performance of dynamic studies. Further improvement of the coil design with regard to flexibility is hoped to enable the visualization of urethral displacement during straining which would add valuable dynamic information to the achieved static high-resolution imaging of this region.

The acquired T2-weighted axial images enabled the visualization of four layers of the urethra in high-resolution. The fluid filled urethral lumen had a bright signal. The mucosa of the urethra was also hyperintense on T2-weighted images and indistinguishable from the fluid. The circumferential hypointense layer surrounding the lumen is believed to correspond to the submucosa. The hyperintense region encircling the submucosal vasculature layers corresponds to the smooth muscle (longitudinal and circular) layers in a very loose connective tissue-matrix that enclose the urethra. The hypointense layer, surrounding the smooth muscle layers, represented a dense connective-tissue layer, with varying amounts of striated urogenital sphincter muscle.

The proposed image intensity correction algorithm applies a theoretical model of the current distribution and requires interactive positioning of the coil conductors from the user, thus potentially making the resulting corrected images prone to systematic or user dependent errors. The application of the IIC however, reliably removed signal inhomogeneities and hot spots due to the coil conductors, thus facilitating the visualization of structures adjacent to the coil. Tissue contrast was successfully regained after image correction. Interactive displacement of the coil conductors did not, or just minimally, affect the outcome. The employed IIC is therefore considered to be robust for the intraurethral applications.

In one set of studies, the performance of a coil system according to the present invention was evaluated in one formalin fixed and in six freshly harvested female human cadaver pelvises. The coils were introduced into the urethra with the tip entering about 5 mm into the bladder. This position insured that the entire urethra was covered by the highest signal intensity and homogeneity of the coil. Imaging was performed on a 1.5 T Signa LX-2 EchoSpeed (GE Medical Systems, Milwaukee Wis.). High-resolution fast spin-echo (FSE) T2-weighted imaging of the whole urethra was acquired axial to the urethra coil. Imaging parameters were: FSE 8 echoes; TR/TE 2000/78 ms; FOV 30×30 mm; matrix 320×192; 6 NEX; BW 15.6 kHz; slice 1.5 mm; imaging time 4:48 minutes. For high-resolution imaging, the in-plain resolution was increased by reducing the FOV to 20×20 mm and using a 256×256 matrix. Imaging time was 8:32 minutes with 8NEX. An image intensity correction (IIC) algorithm was applied to compensate for the B1 signal variation of the coils across the small FOVs. The applied postprocessing method allow the coil position and angle to be entered interactively. Histologic correlation of the MR images was achieved by removing the urethra en bloc from the unfixed cadavers. The specimens were fixed by suspension in 10 percent buffered formalin. They were then embedded in paraffin and 6 micrometer thick axial sections were cut and stained with Trichrome staining on glass sides.

Results obtained included the following: the quality factor, Q, of the loaded coils was determined to be 67 for the single-loop and 80 and 74 for the quadrature coils, respectively. The impedance of the coaxial chokes was Z equals 750 ohms. The paddle enabled an isolation of both coils of 50 dB without loss of performance. Small FOV (30×30 mm) axial imaging with endo urethral coils enabled the visualization of all layers of the urethra with high-resolution. Signal penetration depth beyond the urethra was sufficient to depict the pubic bone anterior to and the vagina posterior to the urethra. Post-processing and display of the images with IIC reliably removed B-1 inhomogeneities, thus facilitating the visualization of structures adjacent to the coil. Image contrast increased, resulting in better depict ability of the different urethral wall layers. Further decrease of the FOV to 20×20 mm increased the in-plain resolution to 78×78 micrometers, which enabled the resolution of even single folds of the urethral mucosa.

Example 4

Animal Studies

The in vivo imaging performance of the single-loop coil was evaluated in the urethra of a healthy, fully anesthetized female pig weighing 55 kg. The experiment was conducted in accordance with all regulations set forth by institutional and governmental agencies. The imaging coil was inserted into the urethra with the pig lying in the supine position. Following double oblique sagittal and coronal FSPGR localizer imaging with large FOVs, high-resolution PD and $T_2$-weighted imaging of the entire urethra was acquired in a plane axial oblique to the urethra coil.

Heavily $T_2$-weighted axial images of the midurethra, acquired with the single-loop coil in the urethra of a pig, revealed improved tissue contrast when compared to the images of the cadaver experiments. Despite high in-plane spatial resolution of 78×78 μm and image acquisition times of several minutes, the images acquired in vivo were of high quality and free of blurring and motion artifacts.

In conclusion, the experimental data of these studies demonstrates that intraurethral MRI can provide very high-resolution images of the female urethra and surrounding tissues. It may, therefore, become an important adjunct to urethrograpy and functional methods for the diagnostic evaluation of incontinence, thus contributing to surgical planning and facilitation of surgical correction.

It will be understood that embodiments of the invention described above are illustrative of some of the applications and principles of the present invention. Various modifications may be made by those skilled in the art without departing from the spirit and scope of the invention. Accordingly, the invention is not to be limited to the illustrated embodiments provided above, but is to be understood by the claims set forth below, which are to be interpreted as broadly as allowed by law.

What is claimed is:

1. An apparatus for magnetic resonance imaging of an anatomic region of a human pelvis, comprising:

an endourethral magnetic resonance imaging (MRI) coil comprising an antenna;

an interface circuit interposed between the antenna and a MRI machine, said interface circuit being in electrical communication with the antenna and being in electrical communication with the MRI machine, said interface circuit comprising a tuning-matching circuit, a decoupling circuit and a balun circuit;

an endourethral therapeutic system comprising an endourethral delivery device to deliver a mode of therapy transurethrally to an area of the anatomic region imaged by the endourethral imaging system, the mode of therapy comprising electromagnetic radiation including at least one of light energy, light energy produced by a laser, microwave energy, infrared radiation, and ultraviolet radiation; and a housing enveloping the antenna and the endourethral therapeutic system, the housing comprising an elongate member insertable into a urethra of a patient and temporarily retainable in said urethra.

2. The apparatus of claim 1, wherein the antenna resides on a flexible circuit board.

3. The apparatus of claim 1, wherein the interface circuit further comprises a DC regulating circuit.

4. The apparatus of claim 3, wherein at least one of the tuning-matching circuit, the decoupling circuit, the balun circuit and the DC regulating circuit is enclosed within an interface box connected to the antenna by a connector.

5. The apparatus of claim 3, wherein at least one of the tuning-matching circuit, the decoupling circuit, the balun circuit and the DC regulating circuit is enclosed within an interface box connected to the antenna by a wireless connection.

6. The apparatus of claim 1, wherein the antenna is a receive-only coil.

7. The apparatus of claim 1, wherein the tuning-matching circuit comprises at least two sets of capacitors, a first set in series and a second set in parallel.

8. The apparatus of claim 2, wherein at least one of the tuning-matching circuit and the decoupling circuit resides on the flexible circuit board.

9. The apparatus of claim 1, wherein the decoupling circuit comprises a PIN diode.

10. The apparatus of claim 1, wherein the housing is sealed at a distal end.

11. The apparatus of claim 1, wherein the electrical communication between said interface circuit and said MRI machine comprises a wireless connection.

12. An apparatus for magnetic resonance imaging (MRI) of an anatomic region of a human pelvis, comprising:

an endourethral magnetic resonance imaging coil system, comprising a first antenna and a second antenna, wherein said second antenna is oriented at a preselected position with respect to said first antenna;

an interface system interposed between a MRI machine and said first and second antennas, said interface system being in electrical communication with said MRI machine and with each of said first antenna and said second antenna, said interface system comprising a tuning-matching system, a decoupling system and a balun system; and a housing enveloping at least one of said first antenna and said second antenna;

wherein said electrical communication between said interface system and said MRI machine comprises a wireless connection.

13. The apparatus of claim 12, wherein at least one of said first antenna and said second antenna resides on a flexible circuit board.

14. The apparatus of claim 12, wherein the preselected position arranges said first antenna at a preselected angle to said second antenna.

15. The apparatus of claim 14, wherein said preselected angle is about 90 degrees.

16. The apparatus of claim 12, wherein said preselected position produces a quadrature pattern between said first antenna and said second antenna.

17. The apparatus of claim 12, wherein said interface system comprises a first interface circuit and a second interface circuit, said first interface circuit comprising a first tuning-matching circuit, a first decoupling circuit and a first balun, and said second interface circuit comprising a second tuning-matching circuit, a second decoupling circuit and a second balun, said first interface circuit being interposed between said first antenna and the MRI machine and being in electrical communication with said first antenna and said MRI machine, and said second interface circuit being interposed between said second antenna and said MRI machine and being in electrical communication with said second antenna and said MRI machine.

18. The apparatus of claim 12, wherein the endourethral MRI coil system further comprises a decoupling paddle positionable between said first antenna and said second antenna.

19. The apparatus of claim 18, wherein said decoupling paddle is angularly positionable at an angular position about equidistant between said first antenna and said second antenna.

20. The apparatus of claim 18, wherein a position of said decoupling paddle is adjustable by a user of the endourethral MRI coil system.

21. The apparatus of claim 18, wherein the decoupling paddle is formed in a shape substantially similar to at least one of said first antenna and said second antenna.

22. The apparatus of claim 18, wherein the decoupling paddle is substantially similar in at least one dimension to at least one of said first antenna and said second antenna.

23. The apparatus of claim 12, wherein at least one of said first antenna and said second antenna is a receive-only coil.

24. The apparatus of claim 12, wherein said tuning-matching system comprises at least two sets of capacitors, a first set in series and a second set in parallel.

25. The apparatus of claim 12, wherein said decoupling system comprises a PIN diode.

26. The apparatus of claim 12, wherein the housing comprises an insulator layer applied to cover the at least one of said first antenna and said second antenna.

27. The apparatus of claim 12, wherein the housing comprises a hollow tubular member.

28. The apparatus of claim 27, wherein the hollow tubular member is sealed at a distal end.

29. The apparatus of claim 27, wherein the hollow tubular member envelops said first antenna and said second antenna.

30. The apparatus of claim 1, wherein the elongate member is temporarily retained in a preselected position by an inflation of a balloon.

31. The apparatus of claim 1, wherein the antenna resides on a flexible circuit board.

32. The apparatus of claim 1, wherein the electromagnetic radiation comprises light energy.

33. The apparatus of claim 32, wherein the light energy is produced by a laser.

34. The apparatus of claim 1, wherein the electromagnetic radiation comprises microwave energy.

35. The apparatus of claim 1, wherein the electromagnetic radiation comprises infrared radiation.

36. The apparatus of claim 1, wherein the electromagnetic radiation comprises ultraviolet radiation.

37. The apparatus of claim 1, wherein the mode of therapy further comprises a pharmacologic agent.

38. The apparatus of claim 37, wherein the pharmacologic agent comprises a radiation source.

39. The apparatus of claim 1, wherein the mode of therapy further comprises an implantable device.

40. The apparatus of claim 1, wherein at least one of said tuning-matching circuit, said decoupling circuit and said balun is enclosed within an interface box connected to the antenna with a connector.

41. The apparatus of claim 1, wherein al least one of said tuning-matching circuit, said decoupling circuit and said balun is enclosed within an interface box connected to the antenna with a wireless connection.

42. The apparatus of claim 31, wherein at least one of said tuning-matching circuit, said decoupling circuit and said balun resides on said flexible circuit board.

43. The apparatus of claim 1, wherein the electrical communication between said interface circuit and said MRI machine comprises a wireless connection.

44. The apparatus of claim 1, wherein said endourethral therapeutic system is affixed to an outside surface of the elongate member.

45. The apparatus of claim 44, wherein said endourethral therapeutic system is temporarily affixed to said outside surface and is displaceable therefrom.

46. The apparatus of claim 1, wherein said endourethral therapeutic system is contained within a surrounding layer applied external to the elongate member.

47. The apparatus of claim 1, wherein said endourethral therapeutic system is contained within said elongate member.

48. The apparatus of claim 1, wherein said elongate member comprises a hollow tubular member.

49. The apparatus of claim 48, wherein said endourethral therapeutic system is contained within said hollow tubular member.

50. The apparatus of claim 49, wherein said endourethral therapeutic system is displaceable from a first position within said hollow tubular member to a second position external to said hollow tubular member.

51. The apparatus of claim 50, wherein said delivery device, upon the positioning of the endotherapeutic system in said second position, is activated for delivering the mode of therapy.

52. A method for treating an anatomic region within a pelvis of a patient, comprising:
providing an apparatus as defined by claim 1;
providing the MRI machine;
inserting said elongate member into the urethra of said patient;
temporarily retaining said elongate member in said urethra;
positioning the pelvis of the patient in a diagnostically effective position relative to the MRI machine;
using the MRI machine to excite magnetic resonance signals within tissues surrounding the anatomic region;
applying gradient magnetic pulses to said human pelvis to spatially encode the magnetic resonance signals;
receiving said magnetic resonance signals in said endourethral MRI coil and producing responsive output signals therefrom;
processing said output signals to obtain an image of the anatomic region;
identifying an area of the anatomic region to be treated;
positioning the endourethral therapeutic system in therapeutic proximity to the area; and
delivering transurethrally the mode of therapy to said area using said transurethral delivery device.

53. The method of claim 52, further comprising obtaining a post-therapeutic image of the area.

54. The method of claim 51, wherein the step of obtaining the post-therapeutic image of the area is performed using said endourethral imaging system.

55. A method of examining an anatomic region of a human pelvis, comprising:
providing an apparatus as defined by claim 1;
providing the MRI machine;
inserting the endourethral MRI coil into a human urethra;
situating the human pelvis within a main magnetic field of the MRI machine;
imposing said main magnetic field on the human pelvis;
applying RF pulses to said human pelvis to excite magnetic resonance signals within the human pelvis;
applying gradient magnetic pulses to said human pelvis to spatially encode the magnetic resonance signals;
receiving said magnetic resonance signals in said endourethral MRI coil;
emitting responsive output signals from said endourethral MRI coil; and
processing said output signals and converting them into information about the anatomic region of the human pelvis, thereby to examine said anatomic region.

56. A method of diagnosing an abnormality of a prostate of a patient, comprising:
providing an apparatus as defined by claim 1;
providing the MRI machine;
inserting the endourethral MRI coil into a prostatic urethra;
situating the prostate of the patient within a main magnetic field of the MRI machine;
using the MRI machine to excite magnetic resonance signals within tissues surrounding the prostatic urethra;
applying gradient magnetic pulses to said prostate to spatially encode the magnetic resonance signals;
receiving said magnetic resonance signals in said endourethral MRI coil and producing responsive output signals therefrom;

processing said output signals to obtain data about the tissues surrounding the prostatic urethra; and evaluating said data to diagnose the abnormality of the prostate.

57. A method of diagnosing an abnormality of a pelvic floor of a female patient, comprising:

providing an apparatus as defined by claim 1;

providing the MRI machine;

inserting said endourethral MRI coil into a female urethra;

situating said pelvic floor within a main magnetic field of the MRI machine;

using the MRI machine to excite magnetic resonance signals within tissues surrounding the female urethra;

applying gradient magnetic pulses to the tissues surrounding the female urethra to spatially encode the magnetic resonance signals;

receiving said magnetic resonance signals in said endourethral coil and producing responsive output signals therefrom;

processing said output signals to obtain data about the tissues surrounding the female urethra; and evaluating said data to diagnose the abnormality of the female pelvic floor.

58. A method of diagnosing a condition of a pelvis of a pediatric patient, comprising:

providing an apparatus as defined by claim 1;

providing the MRI machine;

inserting said endourethral MRI coil into the urethra of the pediatric patient;

situating the pelvis within a main magnetic field of the MRI machine;

using the MRI machine to excite magnetic resonance signals within tissues surrounding the urethra;

applying gradient magnetic pulses to said human pelvis to spatially encode the magnetic resonance signals;

receiving said magnetic resonance signals in said endourethral MRI coil and producing responsive output signals therefrom;

processing said output signals to obtain data about the tissues surrounding the urethra; and evaluating said data to diagnose the condition of the pelvis of the pediatric patient.

59. An apparatus for magnetic resonance imaging of an anatomic region of a human pelvis, comprising:

an endourethral magnetic resonance imaging (MRI) coil comprising an antenna;

an interface circuit interposed between the antenna and a MRI machine, said interface circuit being in electrical communication with the antenna and being in electrical communication with the MRI machine, said interface circuit comprising a tuning-matching circuit, a decoupling circuit, a balun circuit, and a DC regulating circuit; and a housing enveloping the antenna;

wherein at least one of the tuning-matching circuit, the decoupling circuit, the balun circuit, and the DC regulating circuit is enclosed within an interface box connected to the antenna by a wireless connection.

60. An apparatus for magnetic resonance imaging of an anatomic region of a human pelvis, comprising:

an endourethral magnetic resonance imaging (MRI) coil comprising an antenna;

an interface circuit interposed between the antenna and a MRI machine, said interface circuit being in electrical communication with the antenna and being in electrical communication with the MRI machine, said interface circuit comprising a tuning-matching circuit, a decoupling circuit and a balun circuit; and a housing enveloping the antenna;

wherein the electrical communication between said interface circuit and said MRI machine comprises a wireless connection.

61. An apparatus for magnetic resonance imaging of an anatomic region of a human pelvis, comprising:

an endourethral magnetic resonance imaging (MRI) coil comprising an antenna;

an interface circuit interposed between the antenna and a MRI machine, said interface circuit being in electrical communication with the antenna and being in electrical communication with the MRI machine, said interface circuit comprising a tuning-matching circuit, a decoupling circuit and a balun circuit;

an endourethral therapeutic system comprising an endourethral delivery device to deliver a mode of therapy transurethrally to an area of the anatomic region imaged by the endourethral imaging system; and a housing enveloping the antenna and the endourethral therapeutic system, the housing comprising an elongate member insertable into a urethra of a patient and temporarily retainable in said urethra;

wherein at least one of said tuning-matching circuit, said decoupling circuit and said balun is enclosed within an interface box connected to the antenna with a wireless connection.

62. An apparatus for magnetic resonance imaging of an anatomic region of a human pelvis, comprising:

an endourethral magnetic resonance imaging (MRI) coil comprising an antenna;

an interface circuit interposed between the antenna and a MRI machine, said interface circuit being in electrical communication with the antenna and being in electrical communication with the MRI machine, said interface circuit comprising a tuning-matching circuit, a decoupling circuit and a balun circuit;

an endourethral therapeutic system comprising an endourethral delivery device to deliver a mode of therapy transurethrally to an area of the anatomic region imaged by the endourethral imaging system; and a housing enveloping the antenna and the endourethral therapeutic system, the housing comprising an elongate member insertable into a urethra of a patient and temporarily retainable in said urethra;

wherein the electrical communication between said interface circuit and said MRI machine comprises a wireless connection.

* * * * *